United States Patent
Verweij et al.

(10) Patent No.: US 11,401,525 B2
(45) Date of Patent: Aug. 2, 2022

(54) *SOLANACEAE* PLANT RICH IN ANTHOCYANINS CONCENTRATION

(71) Applicant: Enza Zaden Beheer B.V., Enkhuizen (NL)

(72) Inventors: Cornelis Walter Verweij, Enkhuizen (NL); Francesca Margherita Quattrocchio, Amsterdam (NL); Ronald Edwin Koes, Amsterdam (NL); Valentina Passeri, Amsterdam (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 0 days.

(21) Appl. No.: 17/055,698

(22) PCT Filed: May 17, 2018

(86) PCT No.: PCT/EP2018/062999
§ 371 (c)(1),
(2) Date: Nov. 16, 2020

(87) PCT Pub. No.: WO2019/219200
PCT Pub. Date: Nov. 21, 2019

(65) Prior Publication Data
US 2021/0189408 A1  Jun. 24, 2021

(51) Int. Cl.
*C12N 15/82* (2006.01)
*A01H 6/82* (2018.01)

(52) U.S. Cl.
CPC .......... *C12N 15/825* (2013.01); *A01H 6/822* (2018.05); *C12N 15/8218* (2013.01)

(58) Field of Classification Search
None
See application file for complete search history.

(56) References Cited

FOREIGN PATENT DOCUMENTS

| WO | 2009061216 A1 | 5/2009 |
| WO | 2016016208 A1 | 2/2016 |

OTHER PUBLICATIONS

Capsicum annuum ferric reduction oxidase 7, chloroplastic-like, gene LOC107839780, UniProt/EMBL accession No. A0A1U8DV63, published May 10, 2017.*
Passed et al., 2016, New Challenges for the Design of High Value Plant Products: Stabilization of Anthocyanins in Plant Vacuoles, Frontiers in Plant Science 7:153, pp. 1-9.*
Predicted Capsicum annuum ferric reduction oxidase 7, chloroplastic-like, NCBI/GenBank accession No. XP_016538897, published May 5, 2016.*
Olmstead, 2007, A Summary of Molecular Systematic Research in Solanaceae: 1982-2006, Acta Hort. 745, ISHS 2007, pp. 255-268.*
Keskin et al., 2004, A new, structurally nonredundant, diverse data set of protein-protein interfaces and its implications, Protein Science 13: 1043-1055.*
Guo et al., 2004, Protein tolerance to random amino acid change, Proceedings of the National Academy of Sciences USA 101: 9205-9210.*
Thornton et al., 2000, From structure to function: approaches and limitations, Nature Structural Biology, structural genomic supplement, Nov. 2000: 991-994.*
Kiferle et al., "Tomato R2R3-MYB Proteins SlANT1 and SlAN2: Same Protein Activity, Different Roles", PLOS One, Aug. 26, 2015, pp. 1-20, vol. 10, No. 8.
Liu et al., "Anthocyanin Biosynthesis and Degradation Mechanisms in Solanaceous Vegetables: A Review", Frontiers in Chemistry, Mar. 9, 2018, pp. 1-17, vol. 6.
Vlaming et al., "A Gene for Flower Colour Fading in Petunia hybrida", International Journal of Plant Breeding Research, Mar. 1982, pp. 41-46, vol. 61, No. 1.
Wang et al., "Transcriptome Analysis Reveals Candidate Genes Related to Color Fading of 'Red Bartlett' (*Pyrus communis* L.)", Frontiers in Plant Science, Mar. 31, 2017, pp. 1-10, vol. 8.

* cited by examiner

*Primary Examiner* — Bratislav Stankovic
(74) *Attorney, Agent, or Firm* — The Webb Law Firm

(57) ABSTRACT

Described herein are Solanaceae plants for producing fruits rich in anthocyanins concentration, wherein said plant comprises a mutated fading gene. Also described herein is a method of providing a Solanaceae plant for producing fruits rich in anthocyanins concentration.

20 Claims, 4 Drawing Sheets
Specification includes a Sequence Listing.

SEQUENCE LISTING

<160> NUMBER OF SEQ ID NOS: 26

<210> SEQ ID NO 1
<211> LENGTH: 2217
<212> TYPE: DNA
<213> ORGANISM: Capsicum annuum

<400> SEQUENCE: 1

```
atgggtgaac tttcaagcca agaacctctt cttttaaaga aagaaaatga atttaattat      60
ctcaagaaga tacctctttt ggtatcatca acaatcaaag gaataatgtg ggtgatcttc     120
attgcatggg cagctttttt ctttgtgttg cctacagaat ttggaagaga attgcaacat     180
aaaactataa gagccacaaa tggaactctt tttgggacta caggaagcac attcttgtta     240
ttcagtttcc cagttttcat gattgcattt cttggaatta ttcgtctcgt tctctctggt     300
gaagatgaac ctcaagtcaa gaagactgca aaaggtccaa agtttagatt gtggacattc     360
ccggtgctgg tggatggacc atttggtgtt gttacagcta cagaaatgat tggtgttata     420
ctcttctcag tgtacatcgt gtgggctgta ataatgtaca ctatacagaa tgttgacctc     480
ttatccttgt ttgatgcaca cggcatgaaa gagaaaagtg ctttgttgct ggagctgaca     540
ggccttcgtt ttggattcat tggattaatc tgcttagcat ttttgtttct gcctgttgca     600
cgaggttcag ttcttcttcg agctatagat atcccttttg aacatgccac tagatatcat     660
gtttggctgg acatcttac tatggctctt tttactcttc atggtctgtt ctatgtgatt     720
ggctgggcaa tgcggggacg acttgtggaa gaactagttg actggaaaaa cgtaggagtg     780
gccaatcttc caggagttat cagccttgca gctggtttac tgatgtgggt gacttcactt     840
cctggattaa ggagaaaaaa ctttgaactg ttcttctata cacaccaatt gtatgtggtg     900
ttcgtggtat tcctggtctt gcatgttggt gatttcatct tcatgatggc tggagctggg     960
```

-continued

| | |
|---|---|
| atcttcctgt tcatgcttga tcggttcctt agattcttcc agtcaagaaa gactgttgac | 1020 |
| atactttcag ccacatgttt cccttgtgga accgttgaac tcgttatctc aaaacctgca | 1080 |
| aatttagatt acaacgccct tggctggata ttcttacaaa tacgcgagtt gtcctggctg | 1140 |
| cagtggcacc ctttcagtgt ctcatctagt ccccttgatg ggaaacagca tcttgctatt | 1200 |
| ctgataaagg ttcttggaga ttggacagag aaactgaagg gaaacatctt gaatctttct | 1260 |
| gtagagcaat ctgagacgga gccgcttttg cagcataaca ggaaaataac agcttctgtt | 1320 |
| gaaggtcctt atggacatga atcaccatac cacttaacgt atgaaaatct cattttggta | 1380 |
| gcaggtggaa ttgaatttc tcccttteta gctatcctga gtgatattct ccaccatatc | 1440 |
| aatgatggca agccttgtct gtcaagaaat atactgatag tatgggctat caaaaattcg | 1500 |
| gacgagcttc cacttcttga tacagttgac atggaggcaa tctgtccact tttctctgat | 1560 |
| aaactgaatc ttgagcttca aacatttgtg actcgggaat cacagcctcc attggaggag | 1620 |
| ggtaaaacac ccaaagcaat gcaaccctca atctcccctg gcttcaaggg atgccgaatg | 1680 |
| tctggtttgg ttggtactgg aaatattgta tggtctggat tatatgtcgt agtatccacc | 1740 |
| atagggttgg tgatcactac agcgtcgctg aacattttct acgtaaatcc attcaatgta | 1800 |
| tattattggt ggtacaaagg cttttgttg attggatgca tggctgcaag cattcttata | 1860 |
| tttggtggtc tcgtgatcgc tttatggcat ctttgggaaa ggaaaacctc atcgaaggag | 1920 |
| gaaccagagg acgacacaaa gaaagttgac atcctgcagc accagaatga agcctcttta | 1980 |
| cccaagagtt ttggagaggc tcgatttgtc aacaatattc gatatggtca aagaccggat | 2040 |
| ttccaagaga tatttggatc gcatgcaaag agctgggaa gtgtagatat tggtgtgatt | 2100 |
| gtgtgtggtc ctcctactct tcagactagt gttgctaaag agtgcagaag cagaacttg | 2160 |
| cagagaagag gccatcaggc tatttttccat ttcaacagcc acagttttga cctctag | 2217 |

<210> SEQ ID NO 2
<211> LENGTH: 738
<212> TYPE: PRT
<213> ORGANISM: Capsicum annuum

<400> SEQUENCE: 2

Met Gly Glu Leu Ser Ser Gln Glu Pro Leu Leu Lys Lys Glu Asn
1               5                   10                  15

Glu Phe Asn Tyr Leu Lys Lys Ile Pro Leu Leu Val Ser Ser Thr Ile
            20                  25                  30

Lys Gly Ile Met Trp Val Ile Phe Ile Ala Trp Ala Ala Phe Phe Phe
        35                  40                  45

Val Leu Pro Thr Glu Phe Gly Arg Glu Leu Gln His Lys Thr Ile Arg
    50                  55                  60

Ala Thr Asn Gly Thr Leu Phe Gly Thr Thr Gly Ser Thr Phe Leu Leu
65                  70                  75                  80

Phe Ser Phe Pro Val Phe Met Ile Ala Phe Leu Gly Ile Ile Arg Leu
                85                  90                  95

Val Leu Ser Gly Glu Asp Glu Pro Gln Val Lys Lys Thr Ala Lys Gly
            100                 105                 110

Pro Lys Phe Arg Leu Trp Thr Phe Pro Val Leu Val Asp Gly Pro Phe
        115                 120                 125

Gly Val Val Thr Ala Thr Glu Met Ile Gly Val Ile Leu Phe Ser Val
    130                 135                 140

Tyr Ile Val Trp Ala Val Ile Met Tyr Thr Ile Gln Asn Val Asp Leu

-continued

```
        145                 150                 155                 160
Leu Ser Leu Phe Asp Ala His Gly Met Lys Glu Lys Ser Ala Leu Leu
                165                 170                 175
Leu Glu Leu Thr Gly Leu Arg Phe Gly Phe Ile Gly Leu Ile Cys Leu
            180                 185                 190
Ala Phe Leu Phe Leu Pro Val Ala Arg Gly Ser Val Leu Leu Arg Ala
        195                 200                 205
Ile Asp Ile Pro Phe Glu His Ala Thr Arg Tyr His Val Trp Leu Gly
    210                 215                 220
His Leu Thr Met Ala Leu Phe Thr Leu His Gly Leu Phe Tyr Val Ile
225                 230                 235                 240
Gly Trp Ala Met Arg Gly Arg Leu Val Glu Glu Leu Val Asp Trp Lys
                245                 250                 255
Asn Val Gly Val Ala Asn Leu Pro Gly Val Ile Ser Leu Ala Ala Gly
            260                 265                 270
Leu Leu Met Trp Val Thr Ser Leu Pro Gly Leu Arg Arg Lys Asn Phe
        275                 280                 285
Glu Leu Phe Phe Tyr Thr His Gln Leu Tyr Val Val Phe Val Val Phe
    290                 295                 300
Leu Val Leu His Val Gly Asp Phe Ile Phe Met Met Ala Gly Ala Gly
305                 310                 315                 320
Ile Phe Leu Phe Met Leu Asp Arg Phe Leu Arg Phe Phe Gln Ser Arg
                325                 330                 335
Lys Thr Val Asp Ile Leu Ser Ala Thr Cys Phe Pro Cys Gly Thr Val
            340                 345                 350
Glu Leu Val Ile Ser Lys Pro Ala Asn Leu Asp Tyr Asn Ala Leu Gly
        355                 360                 365
Trp Ile Phe Leu Gln Ile Arg Glu Leu Ser Trp Leu Gln Trp His Pro
    370                 375                 380
Phe Ser Val Ser Ser Pro Leu Asp Gly Lys Gln His Leu Ala Ile
385                 390                 395                 400
Leu Ile Lys Val Leu Gly Asp Trp Thr Glu Lys Leu Lys Gly Asn Ile
                405                 410                 415
Leu Asn Leu Ser Val Glu Gln Ser Glu Thr Glu Pro Leu Leu Gln His
            420                 425                 430
Asn Arg Lys Ile Thr Ala Ser Val Glu Gly Pro Tyr Gly His Glu Ser
        435                 440                 445
Pro Tyr His Leu Thr Tyr Glu Asn Leu Ile Leu Val Ala Gly Gly Ile
    450                 455                 460
Gly Ile Ser Pro Phe Leu Ala Ile Leu Ser Asp Ile Leu His His Ile
465                 470                 475                 480
Asn Asp Gly Lys Pro Cys Leu Ser Arg Asn Ile Leu Ile Val Trp Ala
                485                 490                 495
Ile Lys Asn Ser Asp Glu Leu Pro Leu Leu Asp Thr Val Asp Met Glu
            500                 505                 510
Ala Ile Cys Pro Leu Phe Ser Asp Lys Leu Asn Leu Glu Leu Gln Thr
        515                 520                 525
Phe Val Thr Arg Glu Ser Gln Pro Pro Leu Glu Glu Gly Lys Thr Pro
    530                 535                 540
Lys Ala Met Gln Pro Ser Ile Ser Pro Gly Phe Lys Gly Cys Arg Met
545                 550                 555                 560
Ser Gly Leu Val Gly Thr Gly Asn Ile Val Trp Ser Gly Leu Tyr Val
                565                 570                 575
```

```
Val Val Ser Thr Ile Gly Leu Val Ile Thr Thr Ala Ser Leu Asn Ile
            580                 585                 590

Phe Tyr Val Asn Pro Phe Asn Val Tyr Tyr Trp Tyr Lys Gly Leu
        595                 600                 605

Leu Leu Ile Gly Cys Met Ala Ala Ser Ile Leu Ile Phe Gly Gly Leu
    610                 615                 620

Val Ile Ala Leu Trp His Leu Trp Glu Arg Lys Thr Ser Ser Lys Glu
625                 630                 635                 640

Glu Pro Glu Asp Asp Thr Lys Lys Val Asp Ile Leu Gln His Gln Asn
                645                 650                 655

Glu Ala Ser Leu Pro Lys Ser Phe Gly Glu Ala Arg Phe Val Asn Asn
            660                 665                 670

Ile Arg Tyr Gly Gln Arg Pro Asp Phe Gln Glu Ile Phe Gly Ser His
        675                 680                 685

Ala Lys Ser Trp Gly Ser Val Asp Ile Gly Val Ile Val Cys Gly Pro
    690                 695                 700

Pro Thr Leu Gln Thr Ser Val Ala Lys Glu Cys Arg Arg Gln Asn Leu
705                 710                 715                 720

Gln Arg Arg Gly His Gln Ala Ile Phe His Phe Asn Ser His Ser Phe
                725                 730                 735

Asp Leu

<210> SEQ ID NO 3
<211> LENGTH: 2223
<212> TYPE: DNA
<213> ORGANISM: Solanum lycopersicum

<400> SEQUENCE: 3
atgggtgaac tctcaagcca agaacctctt cttttgaaaa agaaaatga  atttgattct     60 ctcagaaaga caccattttt aatctcatca acaaagttga ttctcaaagt attaatgtgg    120
gtgattttta tttcatgggc tgcttttatt ttcttgttgc caacaaagtt cactaatgaa    180
atttttggga caattgttgg agccaccaaa ggatctattt tcggacagc aggtagcaca    240 tccttgttat tcagtttccc aattatcatg attgcatttc ttgcaattat tcttctcgtt    300
gtctcgggtg aagatcaacc tcaaatcaag aaggctggta aaggaccaac ttttagatta    360
tggacattcc ctgtgctggt ggatggacca tttggggttg ttacagctgc ggaaatgatt    420
ggcgttataa tcttctcggt ctacatcgtc tgggctgtag ttatgtatag tatacagaat    480
gttgacatct tatctttgta tcatttacca gacatgaaag agagaagtgc taagttgctg    540
gagctgacag gtctccgttt tggattcatt ggattaatct gcttagcgtt tttgtttctg    600
cctgttgcac gtggttcagt tcttcttcga gccatagata tcccttttga acatgccact    660
agatatcatg tttggctggg acatcttact atggctattt ttagccttca tggtctattc    720
tatattattg ctgggcaat tcaagggaga cttttggaag aactagtcgg ctggaaaaac    780
ataggaatag ccaatcttcc aggagttatc agccttttag ctggtttatt gatgtggttg    840
acttcacttc ctggagtaag gagaaaaaac tttgagctgt tcttctatac acaccaattg    900
tatgtggtgt ttgtggtgtt cctggctttg catgttggtg attcgtctt catgatggct    960 ggagctggga tcttcctgtt catgcttgat cggttccta gattcttcca gtcacgaaag   1020
acagttgaca tactttcggc cacatgcttt cctgtggaa ccgttgaact cgttatttca   1080
aaacctgcaa atttacatta caacgctctt ggctggatat tcttacaaat acgcgagttg   1140
```

```
tcctggctgc agtggcaccc tttcagtgtc tcttctagtc cccttgatgg caaacatcat   1200
cttgcgattc tcataaaggt tcttggagat tggactgaaa aactgaaggg aaacatcttg   1260
aatctttctg tagaagaatc tgagacggag cctcttttgc tgcataacag gaaaattaca   1320
gcttctgttg aaggtcctta tggacatgaa tcaccatacc acttaacgta tgaaaatctc   1380
attttggtag caggtggaat tggaatttct cccttcctag ctatcctgag tgatatcctc   1440
caccgtatca acgatagctc gccttgcctg ccaagaaata tactaatagt atgggctatc   1500
aaaaactcag atgagcttcc acttcttgaa acagttgaca tggaggcaat ctgtccactt   1560
ttctctgata aactgaatct tgagattcaa acatatgtga cacgggaatc acagccttca   1620
ttggaggagg gtaaaacacc caaagcaatg caccactcaa tctcccctgg cttcaaagga   1680
tgtcgaatgt ctggtttggt tggtactgga catgtcgtat ggtctggatt atatgtcata   1740
gtatccacca tagggtttgt gatcactgta gcattgctgg acattttcta cataaatcca   1800
ttcaatataa cttactggtg gtacaagggg cttttgttga ttggatgcat gactgcaagt   1860
attcttatat ttgggggttt cgttatcgct ttatggcatc tttgggagag gaaaccctca   1920
tcgaaggagg aaccacagga cgccacaaag aaagctgaca tcttgcagca gaatgaagcc   1980
tctttagaca gtaactttgg agaggctcga tatgttaata atattcgata tggtcaaaga   2040
cctgatttcc aagagatatt tggatcacat gcaagagct ggggaagtgt agatattggt   2100
gtaattgtgt gtggtcctcc tactcttcag tccagtattg ctaaagaatg cagaagccag   2160
aacttgaaga gaagaggtcg tcaggctatt ttccatttca acagccacag ttttgacctc   2220
tag                                                                 2223

<210> SEQ ID NO 4
<211> LENGTH: 740
<212> TYPE: PRT
<213> ORGANISM: Solanum lycopersicum

<400> SEQUENCE: 4

Met Gly Glu Leu Ser Ser Gln Glu Pro Leu Leu Lys Lys Glu Asn
1               5                   10                  15

Glu Phe Asp Ser Leu Arg Lys Thr Pro Phe Leu Ile Ser Thr Lys
                20                  25                  30

Leu Ile Leu Lys Val Leu Met Trp Val Ile Phe Ile Ser Trp Ala Ala
                35                  40                  45

Phe Ile Phe Leu Leu Pro Thr Lys Phe Thr Asn Glu Ile Phe Gly Thr
        50                  55                  60

Ile Val Gly Ala Thr Lys Gly Ser Ile Phe Arg Thr Ala Gly Ser Thr
65                  70                  75                  80

Ser Leu Leu Phe Ser Phe Pro Ile Ile Met Ile Ala Phe Leu Ala Ile
                85                  90                  95

Ile Leu Leu Val Val Ser Gly Glu Asp Gln Pro Gln Ile Lys Lys Ala
                100                 105                 110

Gly Lys Gly Pro Thr Phe Arg Leu Trp Thr Phe Pro Val Leu Val Asp
            115                 120                 125

Gly Pro Phe Gly Val Val Thr Ala Ala Glu Met Ile Gly Val Ile Ile
        130                 135                 140

Phe Ser Val Tyr Ile Val Trp Ala Val Val Met Tyr Ser Ile Gln Asn
145                 150                 155                 160

Val Asp Ile Leu Ser Leu Tyr His Leu Pro Asp Met Lys Glu Arg Ser
                165                 170                 175
```

-continued

```
Ala Lys Leu Leu Glu Leu Thr Gly Leu Arg Phe Gly Phe Ile Gly Leu
            180                 185                 190

Ile Cys Leu Ala Phe Leu Phe Leu Pro Val Ala Arg Gly Ser Val Leu
            195                 200                 205

Leu Arg Ala Ile Asp Ile Pro Phe Glu His Ala Thr Arg Tyr His Val
        210                 215                 220

Trp Leu Gly His Leu Thr Met Ala Ile Phe Ser Leu His Gly Leu Phe
225                 230                 235                 240

Tyr Ile Ile Gly Trp Ala Ile Gln Gly Arg Leu Leu Glu Glu Leu Val
                245                 250                 255

Gly Trp Lys Asn Ile Gly Ile Ala Asn Leu Pro Gly Val Ile Ser Leu
            260                 265                 270

Leu Ala Gly Leu Leu Met Trp Leu Thr Ser Leu Pro Gly Val Arg Arg
        275                 280                 285

Lys Asn Phe Glu Leu Phe Phe Tyr Thr His Gln Leu Tyr Val Val Phe
        290                 295                 300

Val Val Phe Leu Ala Leu His Val Gly Asp Phe Val Phe Met Met Ala
305                 310                 315                 320

Gly Ala Gly Ile Phe Leu Phe Met Leu Asp Arg Phe Leu Arg Phe Phe
                325                 330                 335

Gln Ser Arg Lys Thr Val Asp Ile Leu Ser Ala Thr Cys Phe Pro Cys
            340                 345                 350

Gly Thr Val Glu Leu Val Ile Ser Lys Pro Ala Asn Leu His Tyr Asn
        355                 360                 365

Ala Leu Gly Trp Ile Phe Leu Gln Ile Arg Glu Leu Ser Trp Leu Gln
        370                 375                 380

Trp His Pro Phe Ser Val Ser Ser Pro Leu Asp Gly Lys His His
385                 390                 395                 400

Leu Ala Ile Leu Ile Lys Val Leu Gly Asp Trp Thr Glu Lys Leu Lys
                405                 410                 415

Gly Asn Ile Leu Asn Leu Ser Val Glu Ser Glu Thr Glu Pro Leu
            420                 425                 430

Leu Leu His Asn Arg Lys Ile Thr Ala Ser Val Glu Gly Pro Tyr Gly
        435                 440                 445

His Glu Ser Pro Tyr His Leu Thr Tyr Glu Asn Leu Ile Leu Val Ala
        450                 455                 460

Gly Gly Ile Gly Ile Ser Pro Phe Leu Ala Ile Leu Ser Asp Ile Leu
465                 470                 475                 480

His Arg Ile Asn Asp Ser Ser Pro Cys Leu Pro Arg Asn Ile Leu Ile
                485                 490                 495

Val Trp Ala Ile Lys Asn Ser Asp Glu Leu Pro Leu Leu Glu Thr Val
            500                 505                 510

Asp Met Glu Ala Ile Cys Pro Leu Phe Ser Asp Lys Leu Asn Leu Glu
        515                 520                 525

Ile Gln Thr Tyr Val Thr Arg Glu Ser Gln Pro Ser Leu Glu Glu Gly
        530                 535                 540

Lys Thr Pro Lys Ala Met His His Ser Ile Ser Pro Gly Phe Lys Gly
545                 550                 555                 560

Cys Arg Met Ser Gly Leu Val Gly Thr Gly His Val Val Trp Ser Gly
                565                 570                 575

Leu Tyr Val Ile Val Ser Thr Ile Gly Phe Val Ile Thr Val Ala Leu
            580                 585                 590

Leu Asp Ile Phe Tyr Ile Asn Pro Phe Asn Ile Thr Tyr Trp Trp Tyr
```

```
              595                 600                 605
Lys Gly Leu Leu Leu Ile Gly Cys Met Thr Ala Ser Ile Leu Ile Phe
    610                 615                 620

Gly Gly Phe Val Ile Ala Leu Trp His Leu Trp Glu Arg Lys Thr Ser
625                 630                 635                 640

Ser Lys Glu Glu Pro Gln Asp Ala Thr Lys Lys Ala Asp Ile Leu Gln
                645                 650                 655

Gln Asn Glu Ala Ser Leu Asp Ser Asn Phe Gly Glu Ala Arg Tyr Val
            660                 665                 670

Asn Asn Ile Arg Tyr Gly Gln Arg Pro Asp Phe Gln Glu Ile Phe Gly
        675                 680                 685

Ser His Ala Lys Ser Trp Gly Ser Val Asp Ile Gly Val Ile Val Cys
    690                 695                 700

Gly Pro Pro Thr Leu Gln Ser Ser Ile Ala Lys Glu Cys Arg Ser Gln
705                 710                 715                 720

Asn Leu Lys Arg Arg Gly Arg Gln Ala Ile Phe His Phe Asn Ser His
                725                 730                 735

Ser Phe Asp Leu
            740

<210> SEQ ID NO 5
<211> LENGTH: 2229
<212> TYPE: DNA
<213> ORGANISM: Solanum melongena

<400> SEQUENCE: 5
atgggtgaac tctcaggcca agaaccttta cttttgaaaa agaagaatt  taattatctc      60 aacaagacac cactttgggt gtcatcaaca aagttgattc tcaatgtagt aatttgggtg     120
actttcattg cctgggcagc ttttattttc ttcttgccaa cagaattcac taatgaactg     180
gaagggaaaa ttattaaagc caccaaagga actattttg gactacagg aagcacattc      240 ttgatcttca gtttcccaat tttcttgatt gcatttcttg caattattcg tctcattctc     300
tcgggtgaag aaccccaaat caagaaggct gcaaaaggtc caagatttag attatggaca     360
ttcccagtgc tggtggatgg accatttggt gttgttacag ctgcggaaat gattggcgtt     420
gtactcttct cagtgtacat cgtttgggct gtagttatgt atactataaa ggatattgac     480
ctcttatcct tgtttcatcc aagagacatg aaagagagaa gtgctctgtt tctgaggta      540 acaggcctcc gttttggatt cattggatta atctgcttag cattttgtt tctgcctgtt      600 gcacgtggtt cagttcttct tcgagctata gatatccctt tgaacatgc cactagatat      660 catgtttggc tgggacatct cactatggct ctttttagcc tccatggtct gttctatatg     720
attggctggg caatgcaagg ccgacttgcg gaagaactag ccagctggaa aaacgtagga     780
atagccaatc ttccaggagt gatcagcctt gcagctggtt tattgatgtg ggtgacttca     840
cttcccggat taaggagaaa aaactttgaa ctgttcttct atacgcatca attgtatgtg     900
gtgttcgtgg tgttcctggc cttgcatgtt ggtgatttca tcttcatgat ggctggagct     960
gggatcttcc tgttcatgct tgatcggttc cttagattct tccagtcacg aaagacagtg    1020
gacatacttt cagccaaatg ctttccttgt ggaactgtcg aacttgttat tccaaacct     1080 gcaaatttac attacaactc ccttggctgg atattcttac aaatacgcga gttgtcctgg    1140
ctacagtggc acccttttcag tgtctcctct agtccacttg atgggaaaca tcatcttgca    1200
attctcataa aggttctagg agattggacc gaaaaactga agggaaacat cttaaacctt    1260
```

```
tctgtagaag aatctgagac gaagcctctt ttgcatcata acaggaaaat aacagcttct   1320
gttgaaggtc cttatggtca tgaatcacca taccacttaa cgtataaaaa tctcattttg   1380
gtagcaggtg gaattggaat ttctcccttc ctagctatcc tgagtgatat tctccaccgt   1440
atcaatgata gcactccttg tctgccaaga aatatactaa tagtatgggc tatcaaaaat   1500
tcagatgagc ttccacttct cgagacagtt gacatggagg caatctgtcc acttttctct   1560
gataaactga atcttgaaat tcaaacattt gtgacacggg aatcacagcc ttcattggag   1620
gagggtaaaa cacccaaagc aatgcaaacc ccgtcaatct gccctggctt caagggatgt   1680
caaatgtctg gtttggttgg tactggaaat gttgtatggt ctggattata tgtcatagta   1740
tccaccatag ggttggtgat cactgtagcg ttgctggaca tttactacat aaatccattc   1800
aatgtaactt actggtggta caagggactt ttgttgattg gatgcatgac tgcaagtatt   1860
cttatatttg ggggtttcgt tatcatttta tggcatcttt gggaaaggaa agccccatcg   1920
aaggaggaac cagaggatgc cacacagata gttgacgttt tgcagcagca gcagcagaat   1980
gaagcctctt tacccaagag ttctggagag gctcgatatg ttaataatat tcgatatggt   2040
caaagaccag atttccaaga gatatttgga tcacatgcaa agagttgggg aagtgtagat   2100
ataggtgtga ttgtgtgtgg tcctcctact cttcaatcca gtgttgctaa agagtgcaga   2160
agtcagaact tgcagagaag aggccatcag gctattttcc acttcaacag ccacagtttt   2220
gacctctag                                                           2229
```

<210> SEQ ID NO 6
<211> LENGTH: 742
<212> TYPE: PRT
<213> ORGANISM: Solanum melongena

<400> SEQUENCE: 6

```
Met Gly Glu Leu Ser Gly Gln Glu Pro Leu Leu Lys Lys Glu Glu
1               5                   10                  15

Phe Asn Tyr Leu Asn Lys Thr Pro Leu Trp Val Ser Thr Lys Leu
                20                  25                  30

Ile Leu Asn Val Val Ile Trp Val Thr Phe Ile Ala Trp Ala Ala Phe
            35                  40                  45

Ile Phe Phe Leu Pro Thr Glu Phe Thr Asn Glu Leu Glu Gly Lys Ile
        50                  55                  60

Ile Lys Ala Thr Lys Gly Thr Ile Phe Gly Thr Gly Ser Thr Phe
65                  70                  75                  80

Leu Ile Phe Ser Phe Pro Ile Phe Leu Ile Ala Phe Leu Ala Ile Ile
                85                  90                  95

Arg Leu Ile Leu Ser Gly Glu Glu Pro Gln Ile Lys Lys Ala Ala Lys
            100                 105                 110

Gly Pro Arg Phe Arg Leu Trp Thr Phe Pro Val Leu Val Asp Gly Pro
        115                 120                 125

Phe Gly Val Val Thr Ala Ala Glu Met Ile Gly Val Val Leu Phe Ser
    130                 135                 140

Val Tyr Ile Val Trp Ala Val Val Met Tyr Thr Ile Lys Asp Ile Asp
145                 150                 155                 160

Leu Leu Ser Leu Phe His Pro Arg Asp Met Lys Glu Arg Ser Ala Leu
                165                 170                 175

Phe Leu Glu Val Thr Gly Leu Arg Phe Gly Phe Ile Gly Leu Ile Cys
            180                 185                 190

Leu Ala Phe Leu Phe Leu Pro Val Ala Arg Gly Ser Val Leu Leu Arg
```

```
            195                 200                 205
Ala Ile Asp Ile Pro Phe Glu His Ala Thr Arg Tyr His Val Trp Leu
210                 215                 220

Gly His Leu Thr Met Ala Leu Phe Ser Leu His Gly Leu Phe Tyr Met
225                 230                 235                 240

Ile Gly Trp Ala Met Gln Gly Arg Leu Ala Glu Glu Leu Ala Ser Trp
                245                 250                 255

Lys Asn Val Gly Ile Ala Asn Leu Pro Gly Val Ile Ser Leu Ala Ala
                260                 265                 270

Gly Leu Leu Met Trp Val Thr Ser Leu Pro Gly Leu Arg Arg Lys Asn
                275                 280                 285

Phe Glu Leu Phe Phe Tyr Thr His Gln Leu Tyr Val Val Phe Val Val
290                 295                 300

Phe Leu Ala Leu His Val Gly Asp Phe Ile Phe Met Met Ala Gly Ala
305                 310                 315                 320

Gly Ile Phe Leu Phe Met Leu Asp Arg Phe Leu Arg Phe Phe Gln Ser
                325                 330                 335

Arg Lys Thr Val Asp Ile Leu Ser Ala Lys Cys Phe Pro Cys Gly Thr
                340                 345                 350

Val Glu Leu Val Ile Ser Lys Pro Ala Asn Leu His Tyr Asn Ser Leu
                355                 360                 365

Gly Trp Ile Phe Leu Gln Ile Arg Glu Leu Ser Trp Leu Gln Trp His
370                 375                 380

Pro Phe Ser Val Ser Ser Pro Leu Asp Gly Lys His His Leu Ala
385                 390                 395                 400

Ile Leu Ile Lys Val Leu Gly Asp Trp Thr Glu Lys Leu Lys Gly Asn
                405                 410                 415

Ile Leu Asn Leu Ser Val Glu Glu Ser Glu Thr Lys Pro Leu Leu His
                420                 425                 430

His Asn Arg Lys Ile Thr Ala Ser Val Glu Gly Pro Tyr Gly His Glu
                435                 440                 445

Ser Pro Tyr His Leu Thr Tyr Lys Asn Leu Ile Leu Val Ala Gly Gly
450                 455                 460

Ile Gly Ile Ser Pro Phe Leu Ala Ile Leu Ser Asp Ile Leu His Arg
465                 470                 475                 480

Ile Asn Asp Ser Thr Pro Cys Leu Pro Arg Asn Ile Leu Ile Val Trp
                485                 490                 495

Ala Ile Lys Asn Ser Asp Glu Leu Pro Leu Leu Glu Thr Val Asp Met
                500                 505                 510

Glu Ala Ile Cys Pro Leu Phe Ser Asp Lys Leu Asn Leu Glu Ile Gln
                515                 520                 525

Thr Phe Val Thr Arg Glu Ser Gln Pro Ser Leu Glu Glu Gly Lys Thr
530                 535                 540

Pro Lys Ala Met Gln Thr Pro Ser Ile Cys Pro Gly Phe Lys Gly Cys
545                 550                 555                 560

Gln Met Ser Gly Leu Val Gly Thr Gly Asn Val Val Trp Ser Gly Leu
                565                 570                 575

Tyr Val Ile Val Ser Thr Ile Gly Leu Val Ile Thr Val Ala Leu Leu
                580                 585                 590

Asp Ile Tyr Tyr Ile Asn Pro Phe Asn Val Thr Tyr Trp Trp Tyr Lys
                595                 600                 605

Gly Leu Leu Leu Ile Gly Cys Met Thr Ala Ser Ile Leu Ile Phe Gly
610                 615                 620
```

```
Gly Phe Val Ile Ile Leu Trp His Leu Trp Glu Arg Lys Ala Pro Ser
625                 630                 635                 640

Lys Glu Glu Pro Glu Asp Ala Thr Gln Ile Val Asp Val Leu Gln Gln
            645                 650                 655

Gln Gln Gln Asn Glu Ala Ser Leu Pro Lys Ser Ser Gly Glu Ala Arg
        660                 665                 670

Tyr Val Asn Asn Ile Arg Tyr Gly Gln Arg Pro Asp Phe Gln Glu Ile
    675                 680                 685

Phe Gly Ser His Ala Lys Ser Trp Gly Ser Val Asp Ile Gly Val Ile
690                 695                 700

Val Cys Gly Pro Pro Thr Leu Gln Ser Ser Val Ala Lys Glu Cys Arg
705                 710                 715                 720

Ser Gln Asn Leu Gln Arg Arg Gly His Gln Ala Ile Phe His Phe Asn
            725                 730                 735

Ser His Ser Phe Asp Leu
            740
```

<210> SEQ ID NO 7
<211> LENGTH: 2106
<212> TYPE: DNA
<213> ORGANISM: Petunia axillaris

<400> SEQUENCE: 7

```
atggggcttt tgtggttgt catgtcaacc aacctgagga aagccattgc cttgttcaaa      60
gtcccaggca cgattactgc tactaatgcg agaatggcga gctgcattgg ttactgtgga     120
agcacattct tgattttctg tttcccaatc ttcatgattg catttcttgc cattattcat     180
ctgagtctct ctagtgaaga tgaaccacaa gtgaagaaaa cctcaaaagg tccacgtttt     240
cgcttgtgga cattcccagt tttggttgat ggaccactag gggttgtgac agctgcagaa     300
attattggaa ttatactctt ctgtgtgtat atcatctggg ctgttattgt gtatagtatt     360
caaaacatca caccttata ctcatctgat gtacatactg tgaaagagaa aagtgctttg     420
atgctggagc tcacaggtct tcactttgga tccattggat taatctgctt agcattttg      480
tttctgcccg ttgcaagggg ttcagttctt cttcgagctg tagatatccc ttttgagcac     540
gcaacaagat tcatgttttg gctgggacat ctaacaatgc ttcttttac tcttcatggt     600
ctatcctact tgattagctg ggcaatgcag gggcgtcttg tacatgaaat aatggatttg     660
aacagtacag aagttgtcaa tcttccagga gttatcagcc tagcagctgg tttattgatg     720
tgggtgacat cacttcctgg agttaggaga agaaacttcg aactattctt ctatacgcac     780
caactgtaca atatattcgt tttattcctg gccttgcatg ttggtgattt catcttcatg     840
actgctggtg ctggaatatt cctttcatg cttgatcgct tccttagatt ctgtcagtcg     900
cgatggactg ttgacatact ttcagctaca tgctttccta atggaactgt tgaagttgtt     960
ctttcaaaac tgcaaatctc tcactacagt gcccttagtt gggtatttct tcaagttcgt    1020
gaattatcct ggctgcaatg gcaccctttt agtgtctcgt caagtcctct tgatggaaaa    1080
catcatcttt cagtcctcat aaaagtacta ggagactgga ccgaaaagct gaagggacat    1140
gtcttggatc tttctgtaga acaacctcaa atggagcacc tcttgcagaa tcattgcaag    1200
ataactgctt ctgttgaagg gcttatggg catcaatctc catatcattt gacgtatgaa    1260
aaccttattt tggtggcagg cggcatagga atttcccctt cctagctat cttgagcgat    1320
attctccacc ggattaatga cagcaagcct tgtctgccaa gaaatatttt aatagtgtgg    1380
```

-continued

```
gccgtgaaaa aatcagatga gcttccactt cttgagacaa ttgacatgga ggcaatatgt    1440 ccattttct gtgataaact gaatcttgag attcaaacat ttgttactcg agaagcacaa     1500
ccttcattgg aggagggtac aacactcaag ggtgtaaatc cctctgtttc ccctagcctc    1560
aagggatgtc caatgtctgg tttggttggt acaggaaatg ttatatggtc tggaattat     1620 gtccttgttt ccataattgg catggtgatc actgtggcat tgctagacat ttattacgta    1680
aatccattac attacgggtg gtaccatggg cttctgttaa ttggatgtat ggttgctagt    1740
attgttacct ttggaggtct tgtcattggt ttatggcatc tttgggaaaa gaaaacctca    1800
gtgcaagttg aagcagagga taccaagaag gttaacattc tgcaggagtg tgaggctggc    1860
ctaaacaagc tttccaatct tgtcgaggct cagtctgcta atactatcca atatggtgaa    1920
agaccaaatt ttaaagatat atttggatca tatgcagaga ctggggaag cgttgatatt     1980 ggtgtaatcg tgtgtggtcc tcctaccctc cagtctaccg ttgctaaaga gtgcagaaga    2040
cagaacttga agagaagtgg taatcaggct atattccatt tcaacagcca tagttttgac    2100
ctatag                                                               2106
```

<210> SEQ ID NO 8
<211> LENGTH: 701
<212> TYPE: PRT
<213> ORGANISM: Petunia axillaris

<400> SEQUENCE: 8

```
Met Gly Leu Phe Val Val Met Ser Thr Asn Leu Arg Lys Ala Ile
1               5                   10                  15

Ala Leu Phe Lys Val Pro Gly Thr Ile Thr Ala Thr Asn Ala Arg Met
            20                  25                  30

Ala Ser Cys Ile Gly Tyr Cys Gly Ser Thr Phe Leu Ile Phe Cys Phe
        35                  40                  45

Pro Ile Phe Met Ile Ala Phe Leu Ala Ile Ile His Leu Ser Leu Ser
    50                  55                  60

Ser Glu Asp Glu Pro Gln Val Lys Lys Thr Ser Lys Gly Pro Arg Phe
65                  70                  75                  80

Arg Leu Trp Thr Phe Pro Val Leu Val Asp Gly Pro Leu Gly Val Val
                85                  90                  95

Thr Ala Ala Glu Ile Ile Gly Ile Ile Leu Phe Cys Val Tyr Ile Ile
            100                 105                 110

Trp Ala Val Ile Val Tyr Ser Ile Gln Asn Ile Asn Thr Leu Tyr Ser
        115                 120                 125

Ser Asp Val His Thr Val Lys Glu Lys Ser Ala Leu Met Leu Glu Leu
    130                 135                 140

Thr Gly Leu His Phe Gly Ser Ile Gly Leu Ile Cys Leu Ala Phe Leu
145                 150                 155                 160

Phe Leu Pro Val Ala Arg Gly Ser Val Leu Leu Arg Ala Val Asp Ile
                165                 170                 175

Pro Phe Glu His Ala Thr Arg Tyr His Val Trp Leu Gly His Leu Thr
            180                 185                 190

Met Leu Leu Phe Thr Leu His Gly Leu Ser Tyr Leu Ile Ser Trp Ala
        195                 200                 205

Met Gln Gly Arg Leu Val His Glu Ile Met Asp Leu Asn Ser Thr Glu
    210                 215                 220

Val Val Asn Leu Pro Gly Val Ile Ser Leu Ala Ala Gly Leu Leu Met
225                 230                 235                 240
```

```
Trp Val Thr Ser Leu Pro Gly Val Arg Arg Asn Phe Glu Leu Phe
            245                 250                 255

Phe Tyr Thr His Gln Leu Tyr Ile Ile Phe Val Leu Phe Leu Ala Leu
            260                 265                 270

His Val Gly Asp Phe Ile Phe Met Thr Ala Gly Ala Gly Ile Phe Leu
            275                 280                 285

Phe Met Leu Asp Arg Phe Leu Arg Phe Cys Gln Ser Arg Trp Thr Val
            290                 295                 300

Asp Ile Leu Ser Ala Thr Cys Phe Pro Asn Thr Val Glu Val Val
305                 310                 315                 320

Leu Ser Lys Pro Ala Asn Leu His Tyr Ser Ala Leu Ser Trp Val Phe
            325                 330                 335

Leu Gln Val Arg Glu Leu Ser Trp Leu Gln Trp His Pro Phe Ser Val
            340                 345                 350

Ser Ser Ser Pro Leu Asp Gly Lys His His Leu Ser Val Leu Ile Lys
            355                 360                 365

Val Leu Gly Asp Trp Thr Glu Lys Leu Lys Gly His Val Leu Asp Leu
            370                 375                 380

Ser Val Glu Gln Pro Gln Met Glu His Leu Leu Gln Asn His Cys Lys
385                 390                 395                 400

Ile Thr Ala Ser Val Glu Gly Pro Tyr Gly His Gln Ser Pro Tyr His
            405                 410                 415

Leu Thr Tyr Glu Asn Leu Ile Leu Val Ala Gly Ile Gly Ile Ser
            420                 425                 430

Pro Phe Leu Ala Ile Leu Ser Asp Ile Leu His Arg Ile Asn Asp Ser
            435                 440                 445

Lys Pro Cys Leu Pro Arg Asn Ile Leu Ile Val Trp Ala Val Lys Lys
450                 455                 460

Ser Asp Glu Leu Pro Leu Leu Glu Thr Ile Asp Met Glu Ala Ile Cys
465                 470                 475                 480

Pro Phe Phe Cys Asp Lys Leu Asn Leu Glu Ile Gln Thr Phe Val Thr
            485                 490                 495

Arg Glu Ala Gln Pro Ser Leu Glu Glu Gly Thr Thr Leu Lys Gly Val
            500                 505                 510

Asn Pro Ser Val Ser Pro Ser Leu Lys Gly Cys Pro Met Ser Gly Leu
            515                 520                 525

Val Gly Thr Gly Asn Val Ile Trp Ser Gly Ile Tyr Val Leu Val Ser
            530                 535                 540

Ile Ile Gly Met Val Ile Thr Val Ala Leu Leu Asp Ile Tyr Tyr Val
545                 550                 555                 560

Asn Pro Leu His Tyr Gly Trp Tyr His Gly Leu Leu Ile Gly Cys
            565                 570                 575

Met Val Ala Ser Ile Val Thr Phe Gly Gly Leu Val Ile Gly Leu Trp
            580                 585                 590

His Leu Trp Glu Lys Lys Thr Ser Val Gln Val Glu Ala Glu Asp Thr
            595                 600                 605

Lys Lys Val Asn Ile Leu Gln Glu Cys Glu Ala Gly Leu Asn Lys Leu
            610                 615                 620

Ser Asn Leu Val Glu Ala Gln Ser Ala Asn Thr Ile Gln Tyr Gly Glu
625                 630                 635                 640

Arg Pro Asn Phe Lys Asp Ile Phe Gly Ser Tyr Ala Glu Ser Trp Gly
            645                 650                 655

Ser Val Asp Ile Gly Val Ile Val Cys Gly Pro Pro Thr Leu Gln Ser
```

```
            660             665             670
Thr Val Ala Lys Glu Cys Arg Arg Gln Asn Leu Lys Arg Ser Gly Asn
        675             680             685

Gln Ala Ile Phe His Phe Asn Ser His Ser Phe Asp Leu
        690             695             700

<210> SEQ ID NO 9
<211> LENGTH: 2220
<212> TYPE: DNA
<213> ORGANISM: Petunia axillaris

<400> SEQUENCE: 9
atgggtgaat attcaggcca agaacctctt cttttgaaga agaagatga cttcaactat    60 ctcaagaaga cacccttttg ggtatcatca acaaagttaa ttctcaaagt agtaatgtgg   120
atgatcttca ttgcatgggc aacttttctt ttcttattgc ctgcaaattt catggctgaa   180
ttgcaaggga tatgtgttcg agctaccaag gaaactattt ttggaactac tggaagcata   240
ttcttgatat acagtttccc aattctaata attgcgtttc ttgcaattat tcgtcttgtt   300
ctcactggtg aagatgagcc tacagtgaag aagactacaa aaggaccaag ttttcggttg   360
tggacatttc ctgttttggt ggatggacca tttgggttg ttacagctgc agaaattatt   420
ggagttatac tcttctcagt gtacataatc tgggctgtta ttatgtacac tatacggaat   480
attgacacct tatccgggtt tcacgtagag agacgaataa gaagtgctct gttccttgat   540
ctaactggcc ttcgttttgg attcattgga ttagtgtgct agcatttttt gtttctgcct   600
gttgcacggg gttcagttct tcttcgagct atagatatcc cctttgaaca tgccactaga   660
tatcatgttt ggttgggaca tcttacgatg gctcttttta gccttcatgg tctctgctat   720
gtgattagtt gggcaatgcg agggcgcctt atagaggagc tacttgagtg aaaagcata   780 ggaatagcca atcttcctgg agttatcagc cttgcagctg gtttattgat gtgggtgaca   840
tcacttcctg gtgtaaggag aaaaaacttt gaattgttct tctatacaca ccaattatat   900
gtggtgttcg tggtgttctt tgccttgcat gttggcgact catcttcat gatagctggt   960 gctggaatct tcctgttcat gcttgatcgg ttccttagat tctggcagtc gcggaagact   1020
gttgacatac tttcagccac atgttttcct tgtggaaccg ttgagattgt tcttttcaaaa   1080 cctgcaaatt tacattacaa cgccttggc tggatatttt tacaaatacg cgagttatcc   1140
tggctgcagt ggcacccttt cagtgtctcc tctagtcccc ttgatgggaa acatcatatt   1200
gcaattctca taaaggttct tggagattgg actgagaaac tgaaggggcg tatcttgaat   1260
ctctctgttg agcaatctga gatggagccc cttttgcagc ataacagcaa ataactgca   1320 tctgttgaag gtccttatgg ccatgaatcg ccgtatcatt taacgtatga aaatctcatt   1380
ctggtggcag gtggaatagg aatttcccct ttcctagcta tcctaagtga tatcctccac   1440
cgaatcaatg atagcagacc ttgcttgcca agaaatgtac taatagtgtg gctataaaa   1500 aagacagatg agcttccact tcttgagact gttgacatgc aggcaatctg tccacttttc   1560
tctgataaac tgaatctgga gattcaaaca tttgtgactc gagaatctca gccttcgctg   1620
gaggagggga aaacacccaa agtaatgcac ccctcaatct gtcctggctt caagggatgt   1680
caaatgtcta gtttggttgg tactggaaat gttgtatggt ctggaatata tgtcatagca   1740
tccaccattg ggttggtaat cactgtagca ttgctgaaca ttttctacgt aaatccattc   1800
aatgtatatt actggtggta caaggggctt tgttgattg gatgcatggc tgcaagtgtt   1860
gttatttttg ggggtctagt gattgcctta tggcatcttt gggagaggaa aacgtctttg   1920
```

```
aaggaggaac cagaggacgc caacaagaaa gttgacatcc tgcagcaaaa tgaggccgat    1980
ttacagaaca atcttgaaca agctcgattt gtcaataatg ttcgatacgg tcaaagacca    2040
gatttccaag aaatatttgg atcacatgca aagagttggg gaagtgtaga tattggtgtc    2100
atagtgtgtg gtcctcctac tcttcagacc actgtggcta agagtgcag aagacagaac    2160 ttgcaaagaa gagggcatga ggcaattttc catttcaaca gccacagttt tgacctctag    2220
```

<210> SEQ ID NO 10
<211> LENGTH: 739
<212> TYPE: PRT
<213> ORGANISM: Petunia axillaris

<400> SEQUENCE: 10

```
Met Gly Glu Tyr Ser Gly Gln Glu Pro Leu Leu Lys Lys Glu Asp
1               5                   10                  15

Asp Phe Asn Tyr Leu Lys Lys Thr Pro Phe Trp Val Ser Ser Thr Lys
                20                  25                  30

Leu Ile Leu Lys Val Val Met Trp Met Ile Phe Ile Ala Trp Ala Thr
            35                  40                  45

Phe Leu Phe Leu Leu Pro Ala Asn Phe Met Ala Glu Leu Gln Gly Ile
        50                  55                  60

Cys Val Arg Ala Thr Lys Glu Thr Ile Phe Gly Thr Thr Gly Ser Ile
65                  70                  75                  80

Phe Leu Ile Tyr Ser Phe Pro Ile Leu Ile Ala Phe Leu Ala Ile
                85                  90                  95

Ile Arg Leu Val Leu Thr Gly Glu Asp Glu Pro Thr Val Lys Lys Thr
            100                 105                 110

Thr Lys Gly Pro Ser Phe Arg Leu Trp Thr Phe Pro Val Leu Val Asp
        115                 120                 125

Gly Pro Phe Gly Val Val Thr Ala Ala Glu Ile Ile Gly Val Ile Leu
    130                 135                 140

Phe Ser Val Tyr Ile Ile Trp Ala Val Ile Met Tyr Thr Ile Arg Asn
145                 150                 155                 160

Ile Asp Thr Leu Ser Gly Phe His Val Glu Glu Thr Asn Arg Ser Ala
                165                 170                 175

Leu Phe Leu Asp Leu Thr Gly Leu Arg Phe Gly Phe Ile Gly Leu Val
            180                 185                 190

Cys Leu Ala Phe Leu Phe Leu Pro Val Ala Arg Gly Ser Val Leu Leu
        195                 200                 205

Arg Ala Ile Asp Ile Pro Phe Glu His Ala Thr Arg Tyr His Val Trp
    210                 215                 220

Leu Gly His Leu Thr Met Ala Leu Phe Ser Leu His Gly Leu Cys Tyr
225                 230                 235                 240

Val Ile Ser Trp Ala Met Arg Gly Arg Leu Ile Glu Glu Leu Leu Glu
                245                 250                 255

Trp Lys Ser Ile Gly Ile Ala Asn Leu Pro Gly Val Ile Ser Leu Ala
            260                 265                 270

Ala Gly Leu Leu Met Trp Val Thr Ser Leu Pro Gly Val Arg Arg Lys
        275                 280                 285

Asn Phe Glu Leu Phe Phe Tyr Thr His Gln Leu Tyr Val Val Phe Val
    290                 295                 300

Val Phe Phe Ala Leu His Val Gly Asp Phe Ile Phe Met Ile Ala Gly
305                 310                 315                 320
```

-continued

```
Ala Gly Ile Phe Leu Phe Met Leu Asp Arg Phe Leu Arg Phe Trp Gln
            325                 330                 335

Ser Arg Lys Thr Val Asp Ile Leu Ser Ala Thr Cys Phe Pro Cys Gly
        340                 345                 350

Thr Val Glu Ile Val Leu Ser Lys Pro Ala Asn Leu His Tyr Asn Ala
        355                 360                 365

Leu Gly Trp Ile Phe Leu Gln Ile Arg Glu Leu Ser Trp Leu Gln Trp
        370                 375                 380

His Pro Phe Ser Val Ser Ser Pro Leu Asp Gly Lys His His Ile
385                 390                 395                 400

Ala Ile Leu Ile Lys Val Leu Gly Asp Trp Thr Glu Lys Leu Lys Gly
            405                 410                 415

Arg Ile Leu Asn Leu Ser Val Glu Gln Ser Glu Met Glu Pro Leu Leu
            420                 425                 430

Gln His Asn Ser Lys Ile Thr Ala Ser Val Glu Gly Pro Tyr Gly His
        435                 440                 445

Glu Ser Pro Tyr His Leu Thr Tyr Glu Asn Leu Ile Leu Val Ala Gly
        450                 455                 460

Gly Ile Gly Ile Ser Pro Phe Leu Ala Ile Leu Ser Asp Ile Leu His
465                 470                 475                 480

Arg Ile Asn Asp Ser Arg Pro Cys Leu Pro Arg Asn Val Leu Ile Val
            485                 490                 495

Trp Ala Ile Lys Lys Thr Asp Glu Leu Pro Leu Leu Glu Thr Val Asp
            500                 505                 510

Met Gln Ala Ile Cys Pro Leu Phe Ser Asp Lys Leu Asn Leu Glu Ile
        515                 520                 525

Gln Thr Phe Val Thr Arg Glu Ser Gln Pro Ser Leu Glu Glu Gly Lys
        530                 535                 540

Thr Pro Lys Val Met His Pro Ser Ile Cys Pro Gly Phe Lys Gly Cys
545                 550                 555                 560

Gln Met Ser Ser Leu Val Gly Thr Gly Asn Val Val Trp Ser Gly Ile
            565                 570                 575

Tyr Val Ile Ala Ser Thr Ile Gly Leu Val Ile Thr Val Ala Leu Leu
            580                 585                 590

Asn Ile Phe Tyr Val Asn Pro Phe Asn Val Tyr Tyr Trp Trp Tyr Lys
        595                 600                 605

Gly Leu Leu Leu Ile Gly Cys Met Ala Ala Ser Val Val Ile Phe Gly
        610                 615                 620

Gly Leu Val Ile Ala Leu Trp His Leu Trp Glu Arg Lys Thr Ser Leu
625                 630                 635                 640

Lys Glu Glu Pro Glu Asp Ala Asn Lys Lys Val Asp Ile Leu Gln Gln
            645                 650                 655

Asn Glu Ala Asp Leu Gln Asn Asn Leu Glu Gln Ala Arg Phe Val Asn
        660                 665                 670

Asn Val Arg Tyr Gly Gln Arg Pro Asp Phe Gln Glu Ile Phe Gly Ser
        675                 680                 685

His Ala Lys Ser Trp Gly Ser Val Asp Ile Gly Val Ile Val Cys Gly
        690                 695                 700

Pro Pro Thr Leu Gln Thr Thr Val Ala Lys Glu Cys Arg Arg Gln Asn
705                 710                 715                 720

Leu Gln Arg Arg Gly His Glu Ala Ile Phe His Phe Asn Ser His Ser
            725                 730                 735

Phe Asp Leu
```

<210> SEQ ID NO 11
<211> LENGTH: 2211
<212> TYPE: DNA
<213> ORGANISM: Petunia axillaris

<400> SEQUENCE: 11

| | | | | | |
|---|---|---|---|---|---|
| atgggtgaat | attcaggcca | agaacctctt | cttttgaaga | agaagatga | cttcaactac | 60 |
| ctcaagaaga | caccattttg | gataccatca | acaaagttaa | ttctcaaagt | agtaatgtgg | 120 |
| gtgattttca | ttgcatgggc | aacttttctt | ttcttattgc | ctacaaattt | catgaaagaa | 180 |
| ttgcaagaga | aatgtattga | agccaccaat | ggaactattt | tggggaaac | tggaagcata | 240 |
| ttcttgatgt | tcagtttccc | aattcttata | attgcattcc | ttgcaattat | tcgtctcgct | 300 |
| ctgagtactg | gtgaagatga | acctctagtg | aagaagacag | caaaaggtcc | aaattttcgc | 360 |
| ttatggacat | ttccagtttt | ggtggatgga | ccattagggg | ttgttacagc | tgcagaaatg | 420 |
| attggaatta | ttgtcttctc | ggtgtacata | atctgcgctg | ttattatgta | cactatacgg | 480 |
| aatattgatg | cactatcctg | gtttcattta | gaggaaacga | atagaagtgc | tctatttctg | 540 |
| cagctaacag | gccgtcattt | gggatccatg | ggattagtct | gcttaggatt | tttgtttcta | 600 |
| ccagttgcac | ggggttcagt | tcttcttcga | gctatagata | taccttttga | acatgccatt | 660 |
| agatatcatg | tttggctggg | acatcttact | atggctcttt | ttagccttca | tggtctgttc | 720 |
| tatgtgattg | gctgggcaat | gcgggggcgc | cttgtggaaa | tggtgagcgt | aggagtagcc | 780 |
| catcttccag | gagttatcag | ccttgcagct | ggtttagtga | tgtgggtgac | atcacttcct | 840 |
| ggtgtaagga | gaaaaaactt | tgaattgttc | ttctatacac | accaactata | tgtagtattc | 900 |
| gtggtattcc | tcgccttgca | tgttggtgac | ttcacttttg | tgatagctgg | tgctgggatc | 960 |
| ttcctgttca | tgcttgatcg | gttccttaga | ttctgccagt | cacggaggac | agttgacatt | 1020 |
| ctttcagcca | catgtttacc | ttgtggaacc | attgaagttg | ttcttccaaa | acctgcaaat | 1080 |
| ttacattaca | acgcccttgg | ctggatattt | ttacagatac | gcgagttatc | cttgctgcag | 1140 |
| tggcacccctt | tcagtgtctc | ctctagtcct | cttgatggaa | acatcatat | tgcaattctc | 1200 |
| ataaagggtc | ttggagattg | gactgagaaa | ctgaaggac | gtatcttgaa | tctctctgta | 1260 |
| gagcaatttg | agatggagcc | ccttttgcag | cataacagca | aaataacagc | ttctgttgaa | 1320 |
| ggtccttatg | gccatgaatc | accatatcat | ttaacgtatg | aacatctcat | tttggtagca | 1380 |
| ggcggaattg | gaatttcccc | tttcctagcc | atcctgagcg | atatcctcca | ccgtatcaat | 1440 |
| gatagcagac | cttgcttgcc | aagaaatata | ctaatagtat | gggctataaa | aaagacagat | 1500 |
| gagcttccac | ttcttgagac | actagacatg | gaggcaatct | gtccactttt | ctctgataaa | 1560 |
| ctgaatctgg | agattcaaac | atttgtcact | cgagaatctc | aaccttccgt | ggaggagggt | 1620 |
| aaaacacccca | atgcaatgaa | cacctcaatc | tgcccaggct | tcaaaggatg | tcaaatgtct | 1680 |
| agtttgattg | gtactggaaa | tgttatatgg | tctggattat | atgtcattgt | atccacaatt | 1740 |
| gggttggtga | tcactgtagc | tttactgaac | atcttctaca | taaatccttt | caatgtacat | 1800 |
| tactggtggt | acaaggggct | tttgttgatc | ggatgcatgg | ctgcaagtat | tcttatattt | 1860 |
| gggggtccag | tgatcgcttt | atggcatttt | tgggaaagga | aaaccttatt | gaaggaggaa | 1920 |
| tcagaggatg | tcaaaagaa | ggttgacatc | cagcagcaga | atgaggctag | tttacaaaag | 1980 |
| aatcttgggg | aggctcgata | tgtcaataat | attcgatatg | gtgaaagacc | tgatttccaa | 2040 |
| gaaatatttg | gattacatgc | aaagagttgg | ggaagtgtag | atattggtgt | catagtgtgt | 2100 |

-continued

```
ggtcctccta ctcttcagtc cagtgttgct aaagagtgca gaaggcagaa cttgcaaaga    2160
agagggcatg aggccatttt ccattttaac agccacagtt ttgacctcta g             2211
```

<210> SEQ ID NO 12
<211> LENGTH: 736
<212> TYPE: PRT
<213> ORGANISM: Petunia axillaris

<400> SEQUENCE: 12

```
Met Gly Glu Tyr Ser Gly Gln Glu Pro Leu Leu Lys Lys Glu Asp
1               5                   10                  15

Asp Phe Asn Tyr Leu Lys Lys Thr Pro Phe Trp Ile Pro Ser Thr Lys
            20                  25                  30

Leu Ile Leu Lys Val Val Met Trp Val Ile Phe Ile Ala Trp Ala Thr
        35                  40                  45

Phe Leu Phe Leu Leu Pro Thr Asn Phe Met Lys Glu Leu Gln Glu Lys
    50                  55                  60

Cys Ile Glu Ala Thr Asn Gly Thr Ile Phe Gly Glu Thr Gly Ser Ile
65                  70                  75                  80

Phe Leu Met Phe Ser Phe Pro Ile Leu Ile Ala Phe Leu Ala Ile
                85                  90                  95

Ile Arg Leu Ala Leu Ser Thr Gly Glu Asp Glu Pro Leu Val Lys Lys
                100                 105                 110

Thr Ala Lys Gly Pro Asn Phe Arg Leu Trp Thr Phe Pro Val Leu Val
            115                 120                 125

Asp Gly Pro Leu Gly Val Val Thr Ala Ala Glu Met Ile Gly Ile Ile
130                 135                 140

Val Phe Ser Val Tyr Ile Ile Cys Ala Val Ile Met Tyr Thr Ile Arg
145                 150                 155                 160

Asn Ile Asp Ala Leu Ser Trp Phe His Leu Glu Glu Thr Asn Arg Ser
                165                 170                 175

Ala Leu Phe Leu Gln Leu Thr Gly Arg His Leu Gly Ser Met Gly Leu
            180                 185                 190

Val Cys Leu Gly Phe Leu Phe Leu Pro Val Ala Arg Gly Ser Val Leu
        195                 200                 205

Leu Arg Ala Ile Asp Ile Pro Phe Glu His Ala Ile Arg Tyr His Val
    210                 215                 220

Trp Leu Gly His Leu Thr Met Ala Leu Phe Ser Leu His Gly Leu Phe
225                 230                 235                 240

Tyr Val Ile Gly Trp Ala Met Arg Gly Arg Leu Val Glu Met Val Ser
                245                 250                 255

Val Gly Val Ala His Leu Pro Gly Val Ile Ser Leu Ala Ala Gly Leu
            260                 265                 270

Val Met Trp Val Thr Ser Leu Pro Gly Val Arg Arg Lys Asn Phe Glu
        275                 280                 285

Leu Phe Phe Tyr Thr His Gln Leu Tyr Val Val Phe Val Phe Leu
    290                 295                 300

Ala Leu His Val Gly Asp Phe Thr Phe Val Ile Ala Gly Ala Gly Ile
305                 310                 315                 320

Phe Leu Phe Met Leu Asp Arg Phe Leu Arg Phe Cys Gln Ser Arg Arg
                325                 330                 335

Thr Val Asp Ile Leu Ser Ala Thr Cys Leu Pro Cys Gly Thr Ile Glu
            340                 345                 350

Val Val Leu Pro Lys Pro Ala Asn Leu His Tyr Asn Ala Leu Gly Trp
```

```
                355                 360                 365
Ile Phe Leu Gln Ile Arg Glu Leu Ser Leu Leu Gln Trp His Pro Phe
370                 375                 380

Ser Val Ser Ser Pro Leu Asp Gly Lys His His Ile Ala Ile Leu
385                 390                 395                 400

Ile Lys Gly Leu Gly Asp Trp Thr Glu Lys Leu Lys Gly Arg Ile Leu
                405                 410                 415

Asn Leu Ser Val Glu Gln Phe Glu Met Glu Pro Leu Leu Gln His Asn
                420                 425                 430

Ser Lys Ile Thr Ala Ser Val Glu Gly Pro Tyr Gly His Glu Ser Pro
                435                 440                 445

Tyr His Leu Thr Tyr Glu His Leu Ile Leu Val Ala Gly Gly Ile Gly
                450                 455                 460

Ile Ser Pro Phe Leu Ala Ile Leu Ser Asp Ile Leu His Arg Ile Asn
465                 470                 475                 480

Asp Ser Arg Pro Cys Leu Pro Arg Asn Ile Leu Ile Val Trp Ala Ile
                485                 490                 495

Lys Lys Thr Asp Glu Leu Pro Leu Leu Glu Thr Leu Asp Met Glu Ala
                500                 505                 510

Ile Cys Pro Leu Phe Ser Asp Lys Leu Asn Leu Glu Ile Gln Thr Phe
                515                 520                 525

Val Thr Arg Glu Ser Gln Pro Ser Val Glu Glu Gly Lys Thr Pro Asn
530                 535                 540

Ala Met Asn Thr Ser Ile Cys Pro Gly Phe Lys Gly Cys Gln Met Ser
545                 550                 555                 560

Ser Leu Ile Gly Thr Gly Asn Val Ile Trp Ser Gly Leu Tyr Val Ile
                565                 570                 575

Val Ser Thr Ile Gly Leu Val Ile Thr Val Ala Leu Leu Asn Ile Phe
                580                 585                 590

Tyr Ile Asn Pro Phe Asn Val His Tyr Trp Trp Tyr Lys Gly Leu Leu
                595                 600                 605

Leu Ile Gly Cys Met Ala Ala Ser Ile Leu Ile Phe Gly Gly Pro Val
610                 615                 620

Ile Ala Leu Trp His Phe Trp Glu Arg Lys Thr Leu Leu Lys Glu Glu
625                 630                 635                 640

Ser Glu Asp Val Lys Lys Val Asp Ile Gln Gln Gln Asn Glu Ala
                645                 650                 655

Ser Leu Gln Lys Asn Leu Gly Glu Ala Arg Tyr Val Asn Asn Ile Arg
                660                 665                 670

Tyr Gly Glu Arg Pro Asp Phe Gln Glu Ile Phe Gly Leu His Ala Lys
                675                 680                 685

Ser Trp Gly Ser Val Asp Ile Gly Val Ile Val Cys Gly Pro Pro Thr
690                 695                 700

Leu Gln Ser Ser Val Ala Lys Glu Cys Arg Arg Gln Asn Leu Gln Arg
705                 710                 715                 720

Arg Gly His Glu Ala Ile Phe His Phe Asn Ser His Ser Phe Asp Leu
                725                 730                 735

<210> SEQ ID NO 13
<211> LENGTH: 522
<212> TYPE: DNA
<213> ORGANISM: Capsicum annuum

<400> SEQUENCE: 13
```

| | |
|---|---|
| atgagcaaac ctggttgtga taacaaagag gaaatgcata aaggatcttg gtctaaacaa | 60 |
| gaagatcaaa aactcattga ttatatcact aaacatggtg aaggttgttg gagagattta | 120 |
| cctaaagctg ctggtctact tcgttgcgga aaaagttgta ggctaagatg gatgaattat | 180 |
| cttaacccaa atttaaaaag aggaaatttt tctgaggatg aagatgatct catcatcaag | 240 |
| cttcatgctc ttcttggcaa taggtggtcc ttaatagctg gaagattgcc aggaagaact | 300 |
| gataatgaag tgaagaatta ttggaattcc catttgagaa gaaaacttat aaaaatggga | 360 |
| atcgatccaa aaaatcataa tatttctcat tatcttcgta taaaaagact tgaatatttc | 420 |
| caagaaaatg gcataaaatc agaaaataat gcagtaatat ctgatgctac aagttctaat | 480 |
| tgtgttacaa gttcattgcc tgatcttaat tcacttccat ag | 522 |

<210> SEQ ID NO 14
<211> LENGTH: 173
<212> TYPE: PRT
<213> ORGANISM: Capsicum annuum

<400> SEQUENCE: 14

```
Met Ser Lys Pro Gly Cys Asp Asn Lys Glu Glu Met His Lys Gly Ser
1               5                   10                  15

Trp Ser Lys Gln Glu Asp Gln Lys Leu Ile Asp Tyr Ile Thr Lys His
            20                  25                  30

Gly Glu Gly Cys Trp Arg Asp Leu Pro Lys Ala Ala Gly Leu Leu Arg
        35                  40                  45

Cys Gly Lys Ser Cys Arg Leu Arg Trp Met Asn Tyr Leu Asn Pro Asn
    50                  55                  60

Leu Lys Arg Gly Asn Phe Ser Glu Asp Glu Asp Asp Leu Ile Ile Lys
65                  70                  75                  80

Leu His Ala Leu Leu Gly Asn Arg Trp Ser Leu Ile Ala Gly Arg Leu
                85                  90                  95

Pro Gly Arg Thr Asp Asn Glu Val Lys Asn Tyr Trp Asn Ser His Leu
            100                 105                 110

Arg Arg Lys Leu Ile Lys Met Gly Ile Asp Pro Lys Asn His Asn Ile
        115                 120                 125

Ser His Tyr Leu Arg Ile Lys Arg Leu Glu Tyr Phe Gln Glu Asn Gly
    130                 135                 140

Ile Lys Ser Glu Asn Asn Ala Val Ile Ser Asp Ala Thr Ser Ser Asn
145                 150                 155                 160

Cys Val Thr Ser Ser Leu Pro Asp Leu Asn Ser Leu Pro
                165                 170
```

<210> SEQ ID NO 15
<211> LENGTH: 537
<212> TYPE: DNA
<213> ORGANISM: Solanum lycopersicum

<400> SEQUENCE: 15

| | |
|---|---|
| atgagaaagc cttgttgtga taacaaagaa gaaatgcata aaggagcttg gtctaaacaa | 60 |
| gaagatcaaa aactcattga ttatatcact aaacatggtg aaggttgctg gagaaattta | 120 |
| cctaaagctg ctggcctgct tcgttgtgga aaaagttgta ggctaagatg gatgaattat | 180 |
| cttaatccaa atctaaaaag aggaaatttt tctgaggatg aagatgatct aatcatcaag | 240 |
| cttcatgctc tccttggcaa taggtggtcg ttaatagcag gaagattgcc aggacgaacg | 300 |
| gataatgaag tgaagaatta ttggaattct catttgacaa gaaaacttat aaaaatggga | 360 |

```
attgatccaa aaaatcatag gctatctcat tatcttcaca taaaaagact tgaattactc      420
caagaaaata acacaagatt agaaaatgtt ggagtaatat ctgatgctac aagttcttat      480
gctaataaag atcaacaaat tacaagttca ttgcttgatc tcaatttaat tccatag        537

<210> SEQ ID NO 16
<211> LENGTH: 178
<212> TYPE: PRT
<213> ORGANISM: Solanum lycopersicum

<400> SEQUENCE: 16

Met Arg Lys Pro Cys Cys Asp Asn Lys Glu Glu Met His Lys Gly Ala
1               5                   10                  15

Trp Ser Lys Gln Glu Asp Gln Lys Leu Ile Asp Tyr Ile Thr Lys His
            20                  25                  30

Gly Glu Gly Cys Trp Arg Asn Leu Pro Lys Ala Ala Gly Leu Leu Arg
        35                  40                  45

Cys Gly Lys Ser Cys Arg Leu Arg Trp Met Asn Tyr Leu Asn Pro Asn
    50                  55                  60

Leu Lys Arg Gly Asn Phe Ser Glu Asp Glu Asp Leu Ile Ile Lys
65                  70                  75                  80

Leu His Ala Leu Leu Gly Asn Arg Trp Ser Leu Ile Ala Gly Arg Leu
                85                  90                  95

Pro Gly Arg Thr Asp Asn Glu Val Lys Asn Tyr Trp Asn Ser His Leu
            100                 105                 110

Thr Arg Lys Leu Ile Lys Met Gly Ile Asp Pro Lys Asn His Arg Leu
        115                 120                 125

Ser His Tyr Leu His Ile Lys Arg Leu Glu Leu Leu Gln Glu Asn Asn
    130                 135                 140

Thr Arg Leu Glu Asn Val Gly Val Ile Ser Asp Ala Thr Ser Ser Tyr
145                 150                 155                 160

Ala Asn Lys Asp Gln Gln Ile Thr Ser Ser Leu Leu Asp Leu Asn Leu
                165                 170                 175

Ile Pro

<210> SEQ ID NO 17
<211> LENGTH: 555
<212> TYPE: DNA
<213> ORGANISM: Petunia axillaris

<400> SEQUENCE: 17
atgagaaagg cttgctgtga taacaaggag gaaatgcata gaggagcttg gtctaagcaa       60
gaagaccaga agctcattga ttatatcact aagcatggcg caggttgctg gcgaaattta      120
cctaaagctg ccggtctgct tcgttgcggt aaaagttgca ggctaagatg gatgaattat      180
cttagcccaa accttaaaag aggaaatttt tctgaggatg aagaggatct catcatcaag      240
cttcatgccc tacttggcaa caggtggtct ctaatagcgg gtagattgcc agggcgcact      300
gataatgaag tgaagaacta ttggaattcc catttgagaa gaaaacttat aaaaatggga      360
attgatccaa agaatcatag gtatctcat tatcttcata ggaaaagact tgagtattgg       420
tcagaaaata gcagcagagg aaccgatcat gaagtggtct ctgatgctgg aagttcttgt      480
gcaaaacatc aaccaagttc cttgcctgat ctcaattccc ctccttcaat tcacagttct      540
tgtgcacaac cgtag                                                        555

<210> SEQ ID NO 18
```

```
<211> LENGTH: 184
<212> TYPE: PRT
<213> ORGANISM: Petunia axillaris

<400> SEQUENCE: 18

Met Arg Lys Ala Cys Cys Asp Asn Lys Glu Glu Met His Arg Gly Ala
1               5                   10                  15

Trp Ser Lys Gln Glu Asp Gln Lys Leu Ile Asp Tyr Ile Thr Lys His
            20                  25                  30

Gly Ala Gly Cys Trp Arg Asn Leu Pro Lys Ala Ala Gly Leu Leu Arg
        35                  40                  45

Cys Gly Lys Ser Cys Arg Leu Arg Trp Met Asn Tyr Leu Ser Pro Asn
    50                  55                  60

Leu Lys Arg Gly Asn Phe Ser Glu Asp Glu Asp Leu Ile Ile Lys
65                  70                  75                  80

Leu His Ala Leu Leu Gly Asn Arg Trp Ser Leu Ile Ala Gly Arg Leu
                85                  90                  95

Pro Gly Arg Thr Asp Asn Glu Val Lys Asn Tyr Trp Asn Ser His Leu
            100                 105                 110

Arg Arg Lys Leu Ile Lys Met Gly Ile Asp Pro Lys Asn His Arg Ile
        115                 120                 125

Ser His Tyr Leu His Arg Lys Arg Leu Glu Tyr Trp Ser Glu Asn Ser
    130                 135                 140

Ser Arg Gly Thr Asp His Glu Val Val Ser Asp Ala Gly Ser Ser Cys
145                 150                 155                 160

Ala Lys His Gln Pro Ser Ser Leu Pro Asp Leu Asn Ser Pro Pro Ser
                165                 170                 175

Ile His Ser Ser Cys Ala Gln Pro
            180

<210> SEQ ID NO 19
<211> LENGTH: 21
<212> TYPE: DNA
<213> ORGANISM: Artificial Sequence
<220> FEATURE:
<223> OTHER INFORMATION: CaAN2 Forward Primer

<400> SEQUENCE: 19
agcttctagg caacagatgg t                                        21

<210> SEQ ID NO 20
<211> LENGTH: 20
<212> TYPE: DNA
<213> ORGANISM: Artificial Sequence
<220> FEATURE:
<223> OTHER INFORMATION: CaAN2 Reverse Primer

<400> SEQUENCE: 20
tgtggtgatc ttgagggcag                                          20

<210> SEQ ID NO 21
<211> LENGTH: 22
<212> TYPE: DNA
<213> ORGANISM: Artificial Sequence
<220> FEATURE:
<223> OTHER INFORMATION: CaActin Forward Primer

<400> SEQUENCE: 21
atccctccac ctcttcactc tc                                       22
```

```
<210> SEQ ID NO 22
<211> LENGTH: 26
<212> TYPE: DNA
<213> ORGANISM: Artificial Sequence
<220> FEATURE:
<223> OTHER INFORMATION: CaActin Reverse Primer

<400> SEQUENCE: 22
gccttaacca ttcctgttcc attatc                                        26

<210> SEQ ID NO 23
<211> LENGTH: 20
<212> TYPE: DNA
<213> ORGANISM: Artificial Sequence
<220> FEATURE:
<223> OTHER INFORMATION: CaFA Forward Primer

<400> SEQUENCE: 23
ttgtttctgc ctgttgcacg                                               20

<210> SEQ ID NO 24
<211> LENGTH: 20
<212> TYPE: DNA
<213> ORGANISM: Artificial Sequence
<220> FEATURE:
<223> OTHER INFORMATION: CaFA Reverse Primer

<400> SEQUENCE: 24
aagggaagca tgtggctgaa                                               20

<210> SEQ ID NO 25
<211> LENGTH: 20
<212> TYPE: DNA
<213> ORGANISM: Artificial Sequence
<220> FEATURE:
<223> OTHER INFORMATION: CaDFR Forward Primer

<400> SEQUENCE: 25
agcagacttg accgtggaag                                               20

<210> SEQ ID NO 26
<211> LENGTH: 21
<212> TYPE: DNA
<213> ORGANISM: Artificial Sequence
<220> FEATURE:
<223> OTHER INFORMATION: CaDFR Reverse Primer

<400> SEQUENCE: 26
cttcgttctc agggtccttg g                                             21
```

SOLANACEAE PLANT RICH IN ANTHOCYANINS CONCENTRATION

CROSS-REFERENCE TO RELATED APPLICATION

This application is the United States national phase of International Application No. PCT/EP2018/062999 filed May 17, 2018, the disclosure of which is hereby incorporated by reference in its entirety.

The Sequence Listing associated with this application is filed in electronic format via EFS-Web and is hereby incorporated by reference into the specification in its entirety. The name of the text file containing the Sequence Listing is 2006505_ST25.txt. The size of the text file is 64,695 bytes, and the text file was created on Nov. 5, 2020.

DESCRIPTION

The present invention relates to Solanaceae plants for producing fruits rich in anthocyanins concentration, wherein said plant comprises a mutated fading gene. Furthermore the present invention relates to a method of providing a Solanaceae plant for producing fruits rich in anthocyanins concentration. The plant of present invention is capable of producing mature fruits that are high in anthocyanin concentration. The plants and fruits produced by the plants of present invention have a reduced degradation of anthocyanins during development and ripening of the fruits.

Anthocyanins belong to a class of molecules called flavonoids that are after synthesis in the cytoplasm, sequestered into the vacuole of the plant cells. Structurally, anthocyanins are glycosides and acylglycosides of anthocyanidins and are water-soluble molecules that, depending on their environment and pH, may appear red, purple, or blue. Anthocyanins are present in most flowers of flowering plants but they can also be present in other plant tissues such as leaves, stems, and roots. In Solanaceae crop species, such as pepper, tomato and eggplant, anthocyanins can also be present in the peel and/or flesh of the fruit, giving the fruit a dark coloured—purple-appearance. Depending on the crop, anthocyanin biosynthesis initiates at the start of ripening of the fruits and usually continues throughout the ripening phase. However, anthocyanins disappear during the final step of fruit ripening and the true fruit colour appears and is due to the biosynthesis of other molecules such as carotenoids and lycopenes. For instance in certain pepper varieties, e.g. a red pepper, at the start of ripening, high levels of anthocyanin accumulate in the peel of fruits at the immature stage, giving the fruit a purple appearance, whereas during fruit ripening anthocyanins disappear and the mature red fruit colour appears.

The biosynthesis of anthocyanins occurs through the flavonoid pathway, starting with phenylalanine as a precursor and the production of anthocyanins molecules is further down in the pathway regulated by a conserved protein complex consisting of MYB, bHLH and WD40 proteins. The absence of one or more of the (functional) proteins results in reduction or absence of anthocyanin synthesis. Once anthocyanin molecules are produced, they can be further enzymatically modified involving multiple enzymes such as F3'H, F3' 5'H or glycosyltransferases, resulting in a wide variety of colour due to the chemical structure of the anthocyanin molecules.

Anthocyanins are highly susceptible to (physio) chemical degradation, such as high pH, temperature, light, oxygen, metal ions, affect the colour and stability of anthocyanins. Fully substituted anthocyanins are sensitive to fading whereas plants with simple 3-glycosides modified anthocyanins are less sensitive. Degradation of anthocyanins, a process revert to as fading, occurs in many plant species and in various organs such as flowers, petals and fruits. However, little is known about the biochemical or genetic mechanism of this fading process.

Anthocyanin production is important for the plants as they are involved in many important biological functions in plants such as attraction of pollinators, antioxidant capacity, protection against reactive oxygen species caused by abiotic stresses, protective effects against UV irradiation/DNA damage, and pathogen attack and plant immunity. Furthermore, numerous studies have demonstrated that anthocyanins present in fruits and vegetables are health beneficial due to anti-oxidative, anti-inflammatory, anti-carcinogenic and anti-microbial activities, and may prevent cardiovascular diseases and diabetes in humans. Because of these (health) potential beneficial, understanding the mechanisms related to anthocyanin biosynthesis and anthocyanin stability is very important aspect of currently active fundamental research area but also in crop development. This understanding will be deployed to develop novel crop cultivars with higher anthocyanin content.

Considering the above, there is a need in the art for novel crop cultivars and fruits having increased anthocyanin content and wherein the anthocyanin breakdown (fading of anthocyanin) is avoided and anthocyanin content remains stable during maturation of said crop or fruit. In addition, there is a need in the art for a method to develop novel crops that are less affected by anthocyanin degradation, producing fruits that have high anthocyanin content.

SUMMARY

It is an object of the present invention, amongst other objects, to address the above need in the art. The object of present invention, amongst other objects, is met by the present invention as outlined in the appended claims.

Specifically, the above object, amongst other objects, is met, according to a first aspect, by the present invention by A Solanaceae plant for producing fruits rich in anthocyanins concentration, wherein said plant comprises a fading gene (FA gene) that encodes for a fading protein (FA protein), wherein the FA protein has at least 70% amino acid sequence identity with SEQ ID No.2, and wherein said FA gene comprise a mutation resulting in a reduced expression level or reduced activity of FA protein as compared to a Solanaceae plant wherein no such mutation is present.

The Solanaceae plant wherein no such mutation is present may be a wild type Solanaceae plant or the parent plant. A reduced expression level of FA protein can result in an absence of FA protein. A mutation of the FA gene results in a reduction of FA gene expression and/or reduced FA protein/mRNA levels and the fading of the anthocyanin during maturation of the fruit/flower does not occur. The level of anthocyanin in the fruit (or flower) remains high. This high anthocyanin content is beneficial for plants and its fruits and/or flowers since anthocyanins are important for attraction of pollinators, antioxidant capacity, protection against reactive oxygen species caused by abiotic stresses, protective effects against UV irradiation/DNA damage, and pathogen attack and plant immunity. Furthermore, for food crop it is known that fruits (including vegetables) that are high in anthocyanin content are health beneficial for humans. The fruits are considered herein as substantially mature, harvestable and/or edible fruits.

A fruit is considered a mature fruit wherein during ripening the fruit size increases over time into a fruit having a fruit size that does not significantly increase anymore (mature state). When mature, fruits are harvestable and edible. Therefore the time in which the fruit ripens from unripe to the ripe/mature state is known, or can be determined. In the present invention, the fruit will retain its colour during development and ripening due to the fact that anthocyanin breakdown is avoided and anthocyanin content remains stable during development and maturation of said crop or fruit.

Sequence identity as used herein is defined as the number of identical consecutive aligned nucleotides, or amino acids, over the full length of the present sequences divided by the number of nucleotides, or amino acids, of the full length of the present sequences and multiplied by 100%.

The FA gene was identified in pepper plants (*Capsicum annuum* species) that show fading phenotype in during fruit development. Based on the available genomic sequences the best hit of FA in *Capsicum annuum* species is CA08g13530/Capana08g001718 (CM334 v1.55 and Zunla v2.0, respectively). FA encodes for a protein similar to ferric reduction oxidase, and the genomic region of FA in *Capsicum annuum* is 3522 nucleotides in length, consisting of 9 exons and 8 introns. The coding sequence (cDNA) of the FA gene is 2217 nucleotide and represented by SEQ ID No.1 which encodes a FA protein represented by SEQ ID No.2. The FA gene is a dominant gene expressed in several tissues, such a leaves, petals (only at late stages of development), stems, flowers, fruits, and roots.

The present invention relates to the plant comprising a FA gene, wherein the FA gene encoding for a coding sequence that comprises at least 75% sequence identity with the coding sequence represented by SEQ ID No.1, preferably at least 80% nucleotide sequence identity, more preferably at least 85%, even more preferably at least 95%, preferably at least 99%, most preferably 100% nucleotide sequence identity.

The present invention relates to the plant wherein the FA protein has an amino acid sequence that comprises at least 70% sequence identity with SEQ ID No.2, preferably at least 75% sequence identity, more preferably at least 85% sequence identity, even more preferably at least 95% sequence identity, preferably at least 99% sequence identity, most preferably 100% sequence identity.

The present invention relates to the plant wherein during ripening of fruits of said plant, said fruits have a reduced degradation of anthocyanins in said plant as compared to a wild-type plant wherein no mutation in the FA gene is present. In the present invention, the FA gene is mutated in *Capsicum annuum*, the gene is inactivated by means of reducing its expression. Reducing FA gene expression in pepper fruits prevents the degradation of anthocyanins, thereby resulting in a mature pepper fruit having a high concentration of anthocyanins in its peel resulting in the purple colour of the mature fruit. Mature sweet pepper fruits having a purple colour do not occur in nature, as anthocyanins present in the fruit (peel and flesh) degrade (fade) during ripening of said fruit. The prevention of degradation of anthocyanins in *Capsicum annuum* species by mutation of the FA gene, results in a reduced or absence of FA gene expression and/or reduced mRNA levels and/or a reduced level or absence of FA protein as compared to a wild-type plant wherein no such mutation is present and therefore the fruits will maintain the concentration or level of anthocyanin molecules in the peel during ripening. Therefore mature fruits retain their initial purple colour with a high concentration of anthocyanins present in the peel.

According to another preferred embodiment, the present invention relates to the plant wherein the fruits of said plant are comprised of a peel that is substantially of purple colour or blue colour. In Solanaceae, such as pepper, tomato and eggplant, anthocyanins can give the fruit a dark coloured, purple appearance. At the start of ripening, high levels of anthocyanin accumulate in fruits in the immature stage giving a purple, blue fruit, whereas during fruit ripening anthocyanins disappear and the mature (lycopenes) fruit colour appears, which can be red, yellow orange, white or green, depending on the crop species or crop variety. In case the anthocyanin in the peel of the fruit do not fade and the anthocyanin in the fruit flesh do fade, a fruit can be obtained that has purple skin/peel and red, yellow, orange, white or green coloured fruit flesh. Furthermore, when both in the peel and in the fruit flesh the anthocyanins do not fade a fruit can be obtained that is fully purple/blue coloured, i.e. a mature fruit having high anthocyanin content.

According to yet another preferred embodiment, the present invention relates to the plant wherein fruits of said plant are comprised of a peel and fruit flesh that is substantially of purple and/or blue colour.

According to another preferred embodiment, the present invention relates to the plant, wherein during the development of the fruits of said plant comprise at least 50% higher, more preferably at least 75% higher concentration of anthocyanin in the peel as compared to the peel of the fruits obtained from the Solanaceae plant wherein no such mutation is present. In order to determine the concentration of anthocyanin in fruits, absorption spectroscopy can be performed. The higher the absorption value measured, the higher the concentration of anthocyanins in the fruit.

According to yet another preferred embodiment, the present invention relates to the plant wherein the degradation of anthocyanin during development of the fruits is reduced by at most 50%, preferably at most 40%, more preferably at most 30%, most preferably at most 25%, as compared to the anthocyanin concentration of fruits obtained from the Solanaceae plant wherein no such mutation is present. Degradation of anthocyanins and reduction of the anthocyanin concentration of the mature fruits can be in the fruit flesh or in the peel, or in both the peel and the fruit flesh.

The fading gene is also identified in other Solanaceae plant species. FA gene sequence alignments with SEQ ID No.1 (FA gene of *Capsicum annuum*) were performed using the public databases to investigate if other Solanaceae plant species also have an FA gene or FA orthologue. Next to the pepper plant (*Capsicum annuum*), other plants that contain an FA gene or FA orthologue are tomato plant (*Solanum lycopersicum*) with SEQ ID No.3, eggplant (*Solanum melongena*) with SEQ ID No.5. Petunia plant (*Petunia axillaris*) comprises three FA genes; SEQ ID No.7, SEQ ID No.9 and SEQ ID No.11. Sequence alignments were performed using standard alignment software and by identification of the reciprocal best hit, with pepper plant, tomato plant, eggplant and petunia (See Tables 1 and 2 in the examples).

According to a preferred embodiment, the present invention relates to the plant, wherein the plant is selected from the group consisting of pepper plant (*Capsicum annuum*), tomato plant (*Solanum lycopersicum*), eggplant (*Solanum melongena*) and petunia plant (*Petunia axillaris*).

According to another preferred embodiment, the present invention relates to the plant, wherein the plant is *Capsicum annuum* and said FA gene encodes for a FA protein that has at least 90%, preferably at least 95%, more preferably at least 98%, preferably at least 99%, most preferably 100% amino acid sequence identity with SEQ ID No.2.

According to a yet another preferred embodiment, the present invention relates to the plant, wherein the FA gene comprises a coding sequence that has at least 90%, preferably at least 95%, more preferably at least 98%, preferably at least 99%, most preferably 100% nucleotide sequence identity with SEQ ID No.1.

According to a preferred embodiment, the present invention relates to the plant, wherein the plant is *Solanum lycopersicum* and said FA gene encodes for a FA protein that has at least 90%, preferably at least 95%, more preferably at least 98%, preferably at least 99%, most preferably 100% amino acid sequence identity with SEQ ID No.4.

According to a preferred embodiment, the present invention relates to the plant, wherein the FA gene comprises a coding sequence that has at least 90%, preferably at least 95%, more preferably at least 98%, preferably at least 99%, most preferably 100% nucleotide sequence identity with SEQ ID No.3.

According to a preferred embodiment, the present invention relates to the plant, wherein the plant is *Solanum melongena* and said FA gene encodes for a FA protein that has at least 90%, preferably at least 95%, more preferably at least 98%, preferably at least 99%, most preferably 100% amino acid sequence identity with SEQ ID No.6.

According to a preferred embodiment, the present invention relates to the plant, wherein the FA gene comprises a coding sequence that has at least 90%, preferably at least 95%, more preferably at least 98%, preferably at least 99%, most preferably 100% nucleotide sequence identity with SEQ ID No.5.

According to a yet another preferred embodiment, the present invention relates to the plant, wherein the plant is a *Petunia axillaris* and said FA gene encodes for a FA protein that has at least at least 90%, preferably at least 95%, more preferably at least 98%, preferably at least 99%, most preferably 100% amino acid sequence identity with SEQ ID No.8., SEQ ID No.10, or SEQ ID No.12, preferably SEQ ID No. 8.

According to a preferred embodiment, the present invention relates to the plant, wherein the FA gene comprises a coding sequence that has at least 90%, preferably at least 95%, more preferably at least 98%, preferably at least 99%, most preferably 100% nucleotide sequence identity respectively with SEQ ID No.7, SEQ ID No.9, or SEQ ID No.11, preferably SEQ ID No.7.

Modulating the FA gene to lower its expression can be achieved at various levels. First, the endogenous gene can be directly mutated. This can be achieved by means of a mutagenic treatment. Alternatively, a modified FA gene can be brought into the plant by means of transgenic techniques or by introgression, or the expression of FA can be reduced at the regulatory level, for example by modifying the regulatory sequences or by gene silencing.

The reduced expression level of FA protein is the result of a reduced endogenous FA gene expression and/or reduced mRNA levels. Reducing the expression of the FA gene can be achieved by down-regulation of gene expression either at the transcriptional or the translational level, e.g. by gene silencing or by mutations that affect the expression of the FA gene, either directly, such as by gene silencing, or indirectly by modifying the regulatory sequences thereof, or by stimulating repression of the gene. Regulators can be upregulated (in case of repressor proteins) by transgenic overexpression. Overexpression of the FA gene can be achieved by expressing repressor proteins of the FA gene from a strong promoter, e.g. the 35S promoter that is commonly used in plant biotechnology.

According to a preferred embodiment, the present invention relates to the plant, wherein the mutation in the FA gene encodes an amino acid substitution in the encoded FA protein.

According to another preferred embodiment, the present invention relates to the plant, wherein said mutation is a frameshift mutation or a stop codon mutation in the FA gene.

According to yet another preferred embodiment, the present invention relates to the plant, wherein, wherein said mutation is a non-natural mutation. The down regulation of the FA gene can be achieved by mutagenesis of the coding sequence, regulatory elements in the promoter, terminator region, or potential introns. Mutations in the FA coding sequence in many cases leads to amino acid substitutions or premature stop codons that negatively affect the expression or activity of the encoded FA protein. These mutations can be induced in plants by using mutagenic chemicals such as ethyl methane sulfonate (EMS), by irradiation of plant material with gamma rays or fast neutrons, or mediated by CRISPR/Cas or by other means known in the art to induce mutations in a gene.

The reduced level of FA protein is the result of a mutation in the FA gene resulting in a reduced FA expression as compared to the wild-type FA gene wherein no such mutation is present, or resulting in a reduced mRNA or protein stability. In a particular embodiment this is achieved by mutating the FA coding sequence that results in a non-functional FA protein.

According to yet another preferred embodiment, the present invention relates to the plant, wherein said plant further comprises a mutation in a MYB gene that encodes for a MYB protein resulting in a reduced expression level or reduced activity of MYB protein as compared to a wild-type Solanaceae plant wherein no mutation in the MYB gene is present, wherein the MYB protein has at least 70% sequence identity with SEQ ID No.14. Reducing the specific MYB protein levels will increase anthocyanin production due to an inhibitory function of anthocyanin production of such type of MYB protein. As previously stated, the anthocyanin biosynthesis pathway is regulated by a conserved bHLH/WD40/MYB protein complex. The R2R3MYB proteins function as activators but also repressors, i.e. the MYB protein, which include a C-terminal EAR motif. Constitutively overexpression of MYB in petunia results in no anthocyanin biosynthesis whereas reducing its expression results in increased anthocyanin biosynthesis. These R2R3 MYB repressors are identified in pepper, tomato, and petunia and experiments in which the pepper R2R3MYB repressor expression is reduced by VIGS results in a twofold increased anthocyanin content in immature pepper fruits (See FIG. 4). Therefore, mutation of the MYB gene results in a reduced mRNA expression, and may lead to reduced MYB protein levels and therefore an increase in anthocyanin biosynthesis. Plants having a mutated MYB gene will produce fruits with higher anthocyanin content as compared to fruits of wild type plants (not having a mutation in the MYB gene).

A combination of both a mutated MYB gene and a mutated FA gene results in that the immature fruits will have an increased anthocyanin content due to the reduced or absence of MYB gene expression. Simultaneously, due to the reduced or absence of FA gene expression, there is no fading of the anthocyanin in mature fruits (or immature fruits that are ripening). The mutation of both genes have a synergistic effect resulting in mature fruits that have a high, lasting anthocyanin content as compared to fruits of a wild type plant having no mutations in MYB and FA gene.

According to a preferred embodiment, the present invention relates to the plant, wherein the plant is *Capsicum annuum* and said MYB gene encodes for a MYB protein that has at least 90%, preferably at least 95%, more preferably at least 98%, preferably at least 99%, most preferably 100% amino acid sequence identity with SEQ ID No.14.

According to yet another preferred embodiment, the present invention relates to the plant, wherein the MYB gene comprises a coding sequence that has at least 90%, preferably at least 95%, more preferably at least 98%, preferably at least 99%, most preferably 100% nucleotide sequence identity with SEQ ID No.13.

According to another preferred embodiment, the present invention relates to the plant, wherein the plant is *Solanum lycopersicum* and said MYB gene encodes for a MYB protein that has at least 90%, preferably at least 95%, more preferably at least 98%, preferably at least 99%, most preferably 100% amino acid sequence identity with SEQ ID No.16.

According to yet another preferred embodiment, the present invention relates to the plant, wherein the MYB gene comprises a coding sequence that has at least 90%, preferably at least 95%, more preferably at least 98%, preferably at least 99%, most preferably 100% nucleotide sequence identity with SEQ ID No.15.

According to a preferred embodiment, the present invention relates to the plant, wherein the plant is a petunia plant and said MYB gene encodes for a MYB protein that has at least 90%, preferably at least 95%, more preferably at least 98%, preferably at least 99%, most preferably 100% amino acid sequence identity with SEQ ID No.18.

According to another preferred embodiment, the present invention relates to the plant, wherein the MYB gene comprises a coding sequence that has at least 90%, preferably at least 95%, more preferably at least 98%, preferably at least 99%, most preferably 100% nucleotide sequence identity with SEQ ID No.17.

According to yet another preferred embodiment, the present invention relates to the plant, wherein said mutation in the MYB gene is a non-natural mutation. The mutation of MYB can be effected by gene editing techniques, preferably by CRISPR/Cas and/or mutagenic treatment, in particular with mutagens or radiation.

According to a preferred embodiment, the present invention relates to the plant, wherein the fruits have an increased shelf life. The high concentration of anthocyanin in the mature fruits has a positive effect on its shelf life.

The present invention, according to a second aspect, relates to a method for providing the Solanaceae plant of present invention, comprising the steps of
 a) introducing a mutation in the fading gene (FA gene), wherein said FA gene comprises a coding sequence that has at least 70% nucleotide sequence identity with SEQ ID No.1.
 b) determining a reduction of the endogenous level of FA protein and/or FA mRNA in the plant
 c) selecting the Solanaceae plant that produces fruits that are rich in anthocyanins.

The FA gene to be mutated may have a nucleotide sequence that comprises least 75% nucleotide sequence identity with SEQ ID No.1, preferably at least 80%, more preferably at least 85%, even more preferably 95%, preferably 99%, most preferably 100% nucleotide sequence identity.

According to a preferred embodiment, the present invention relates to the method, wherein step a) further comprises introducing a mutation in the MYB gene, wherein step a) further comprises introducing a mutation in the MYB gene, wherein said MYB gene comprises a coding sequence that has at least 70% nucleotide sequence identity, preferably at least 80%, more preferably at least 85% sequence identity, even more preferably at least 95% sequence identity, preferably at least 99%, most preferably 100% nucleotide sequence identity with SEQ ID No.13.

According to another preferred embodiment, the present invention relates to the method, wherein step b) of the method further comprises determining a reduction of the endogenous level of MYB protein and/or MYB mRNA in the plant. The mutation in the FA gene and/or MYB gene may lead to an amino acid substitution in the encoded protein and/or wherein the mutation in the FA gene and/or MYB gene is a frameshift mutation or a stop codon mutation. The mutation in the FA gene and/or MYB gene is preferably a non-natural mutation.

According to yet another preferred embodiment, the present invention relates to the method, wherein mutation of FA and/or MYB is effected by gene editing techniques, preferably by CRISPR/Cas and/or mutagenic treatment, in particular with mutagens or radiation.

BRIEF DESCRIPTION OF THE FIGURES

The present invention will be further detailed in the following examples and figures wherein.

DETAILED DESCRIPTION

Examples

VIGS Analysis on FA Gene

To investigate if FA is involved in anthocyanin degradation in *Capsicum annuum* a Virus Induced Gene Silencing (VIGS) analysis was performed. A 274 nt fragment (113-384 nt), covering parts of the first and second exon of the FA gene was designed to reduce the endogenous mRNA levels using Tobacco Rattle Virus (TRV) and the VIGS approach. As plants, Mavis and Zulu pepper varieties were used that all show high levels of anthocyanin accumulation in fruits in the immature stage, whereas during fruit ripening anthocyanins degrade and the red mature fruit colour appears. The DNA fragment that was designed to target FA was synthesized and subsequently cloned into a vector. The DNA sequence of FA target sequence was confirmed by Sanger sequencing. The vector contains all sequences encoding for proteins that are required for a functional TRV particles including the FA target sequence. The vector including the FA target sequence (=VIGS construct) is used in VIGS experiments to reduce endogenous mRNA levels in the pepper fruits.

Figure 1:
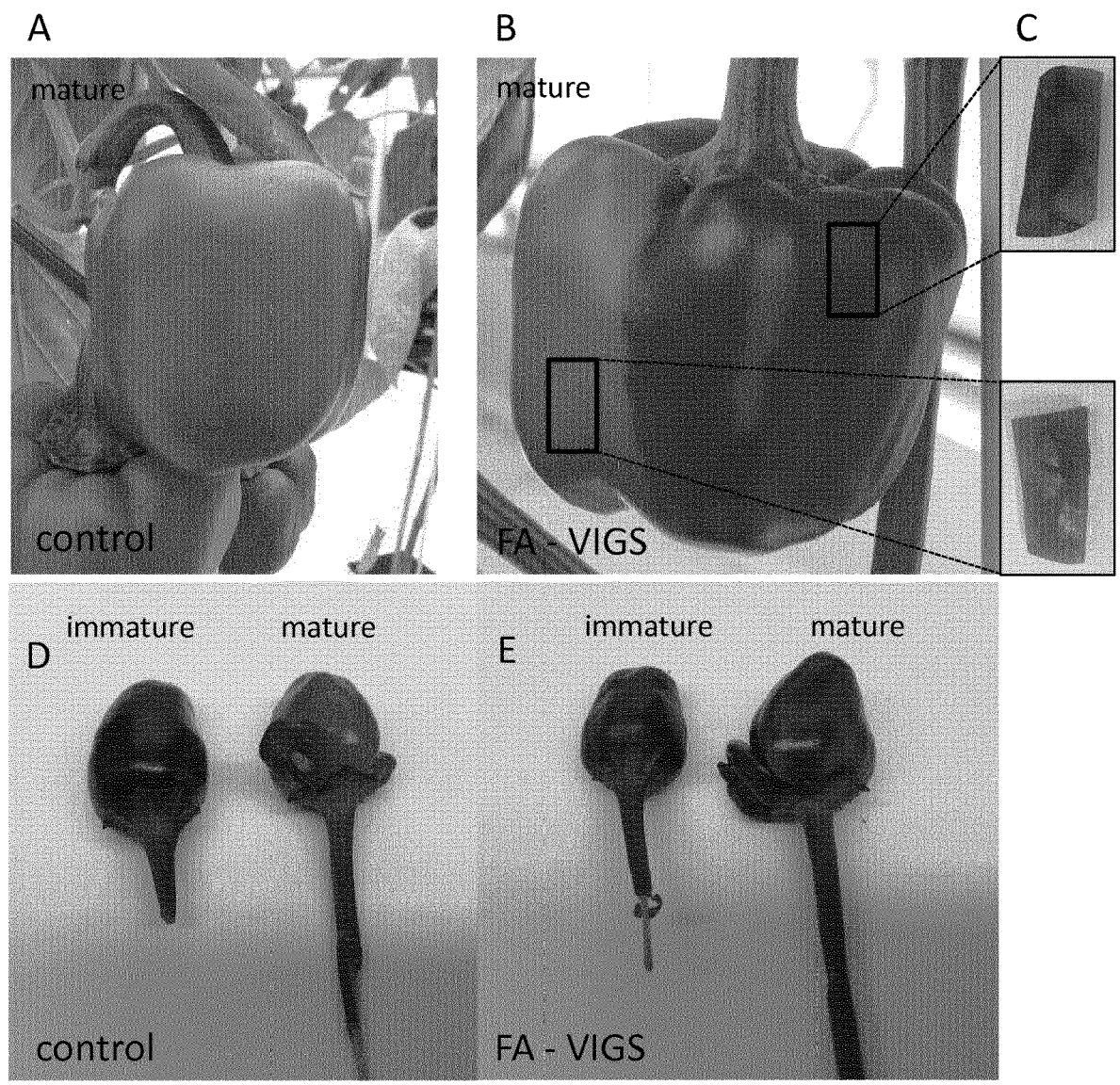
FIG. 1: shows Mavis and Zulu pepper fruit phenotypes. A) Mature fruits phenotype of Mavis control plants. B) Mature fruits of FA-VIGS plants. C) Dissection—partly removing the peel from FA-VIGS fruits (from the fruit shown in B). D) Immature and mature fruits of Zulu control plants. E) Immature and mature fruits of FA-VIGS plants.

Both Mavis and Zulu variety showed, 4 months after agro-infiltration of the VIGS constructs, the purple immature fruits identical to the control plants (FIGS. 1D and E). However, during ripening we observed the appearance of dark (purple) and red coloured patches on the FA-VIGS fruit (FIGS. 1B and E, both FA-VIGS plants) and even when the fruits continue ripening, the purple spots maintained their colour. FIG. 1C shows that the flesh of the fruit is red coloured and that only the peel contains the anthocyanins (the peel is partly removed in the outlined pictures). Based on these results it can be concluded that the purple spots in the peel are the result of the reduced FA expression.

Expression Analysis on FA

To determine whether the mRNA level of FA in FA-VIGS fruits were reduced, expression analysis was performed on the fruits as shown in FIGS. 1D and E. RNA was extracted from the fruits. cDNA synthesis was made from all samples using an oligo-dT oligo method and used as template for the RT-PCR. Fruits at immature and mature stage were harvested and a section of ~1 cm² was cut from the purple and/or red parts of the fruit. Total RNA was extracted using a commercial RNA extraction kit (Machery-Nagel, Nucleospin RNA plant, Bioke, NL) and subsequently, 1 μg total RNA was used for first strand cDNA synthesis. The cDNA was 20× diluted and 5 ul was used as template in the RT-PCR. The following primer sets were used:

| primer | 5'-3' sequence |
|---|---|
| CaAN2-Fwd | AGCTTCTAGG CAACAGATGG T (SEQ ID No. 19) |
| CaAN2-Rev | TGTGGTGATC TTGAGGGCAG (SEQ ID No. 20) |
| CaActin Fwd | ATCCCTCCAC CTCTTCACTC TC (SEQ ID No. 21) |
| CaActin Rev | GCCTTAACCA TTCCTGTTCC ATTATC (SEQ ID No. 22) |
| CaFA-Fwd | TTGTTTCTGC CTGTTGCACG (SEQ ID No. 23) |
| CaFA-Rev | AAGGGAAGCA TGTGGCTGAA (SEQ ID No. 24) |
| CaDFR-Fwd | AGCAGACTTG ACCGTGGAAG (SEQ ID No. 25) |
| CaDFR-Rev | CTTCGTTCTC AGGGTCCTTG G (SEQ ID No. 26) |

Figure 2:
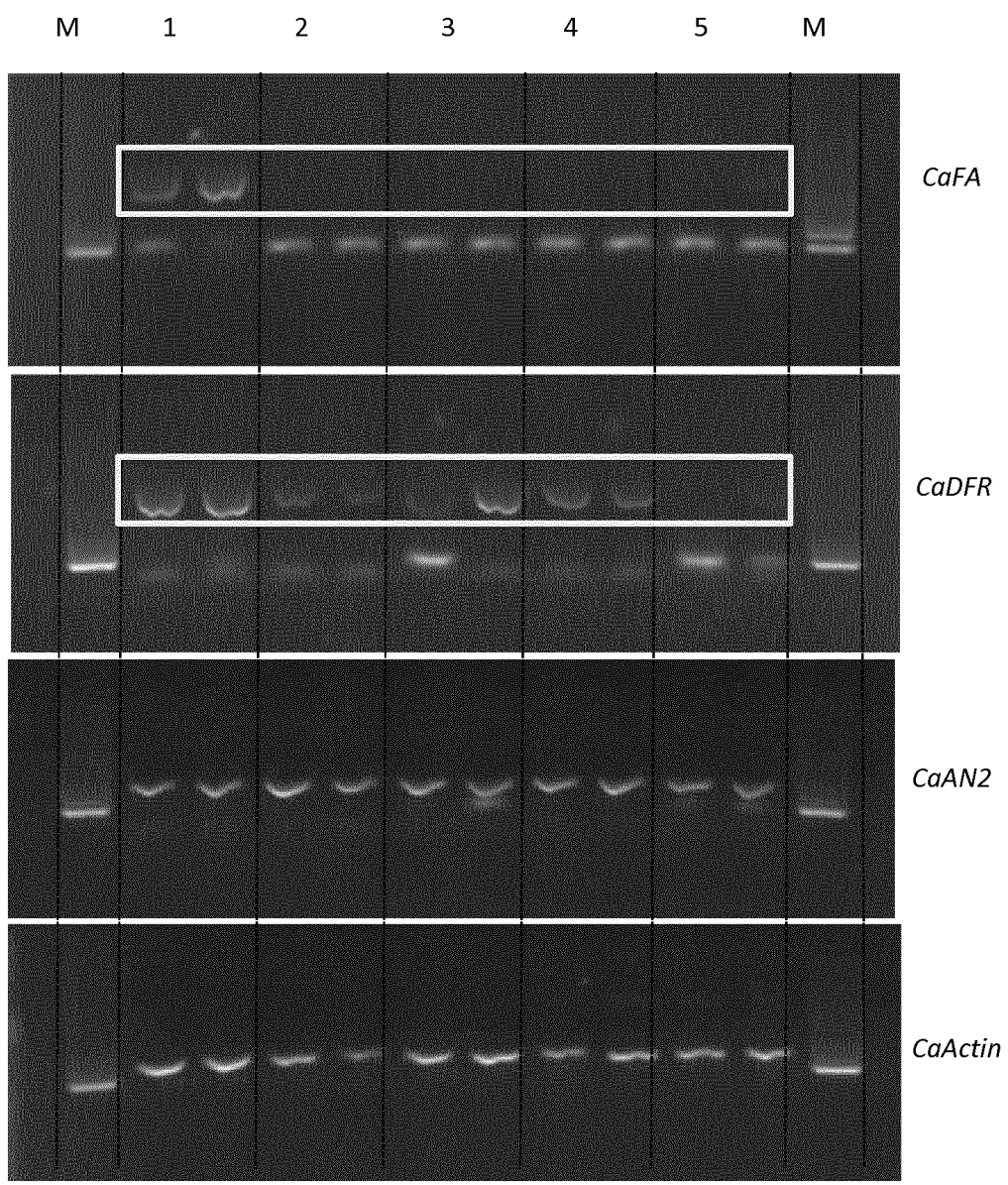
FIG. 2: shows an FA gene expression analysis in fruits obtained from Zulu and Mavis as control and FA-VIGS fruits. A) mRNA expression analysis in Zulu FA VIGS fruits and control fruits (from material shown in FIGS. 1D and E). The *Capsicum annuun* housekeeping gene actin (CaActin) was used to show equal amounts of input material. Furthermore the expression levels of AN2, DFR and FA were determined of pepper, i.e. *Capsicum annuum* (Ca). These genes encode for transcription factors that regulate the anthocyanins biosynthesis. Mutating one of these genes result in no anthocyanins synthesis. Lanes represent; 1=Zulu immature (control), 2=Zulu mature (control), 3=Zulu FA VIGS immature, 4=Zulu FA VIGS mature, 5=Zulu FA VIGS mature. All samples were done in duplicates. The FA gene expression in pepper (CaFA) is reduced (see boxed area) and the CaDFR, CaAN2 genes in the anthocyanin biosynthesis pathway are un-effected, hence anthocyanins are produced at normal levels.

Housekeeping gene actin (CaActin) was used to show equal amounts of input material. Furthermore the expression levels of AN2, DFR and FA were determined. These genes encode for transcription factors that regulate the anthocyanins biosynthesis. Mutating one of these genes results in no anthocyanins synthesis. The expression analysis in FA-VIGS fruits confirmed that the endogenous mRNA levels of FA are reduced, whereas other known anthocyanin related genes such as AN2 and DFR do not show changes in mRNA expression level (FIG. 2).

Results show that FA mRNA is only present in Zulu control fruits and not in FA VIGS fruits, independently from developmental stage, i.e. immature or mature fruits. This confirms that the VIGS approach indeed results in reduced endogenous FA mRNA levels and consequently blocks the degradation of anthocyanins in the peel. The results further indicate that DFR and AN2 expression is independent from the FA expression.

Transgenic Complementation Assay FA Gene in Petunia (by FA Petunia or FA Pepper)

Figure 3:
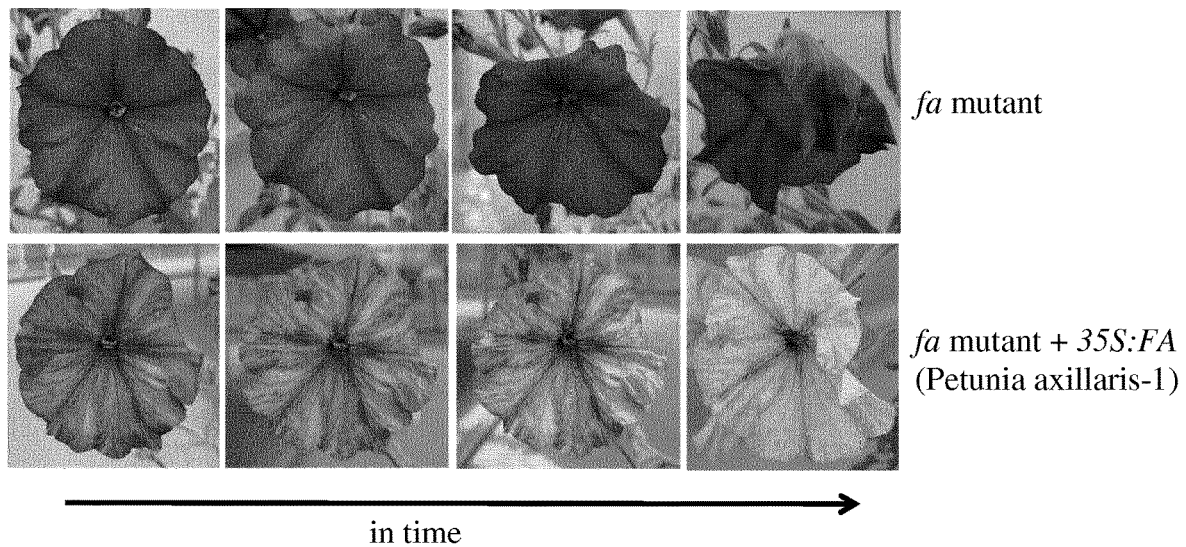
FIG. 3: shows that petunia flower having a mutated FA gene (fa mutant), do not present the fading phenotype because the anthocyanins in the petals are not degraded in time, retaining the flower colour (upper panels). In case the FA mutation is complemented by a construct that expresses the FA gene (35S:FA), i.e. stable transformed plants, the flowers start to fade at early stages of development, loosing their colour (FIG. 3A). Experiments show that the petunia fading phenotype can be complemented by the *Capsicum annuum* FA gene. Results clearly show that the *Capsicum annuum* FA gene (FIG. 3B) and the petunia FA (FIG. 3A) gene are functionally exchangeable.
Figure 3:
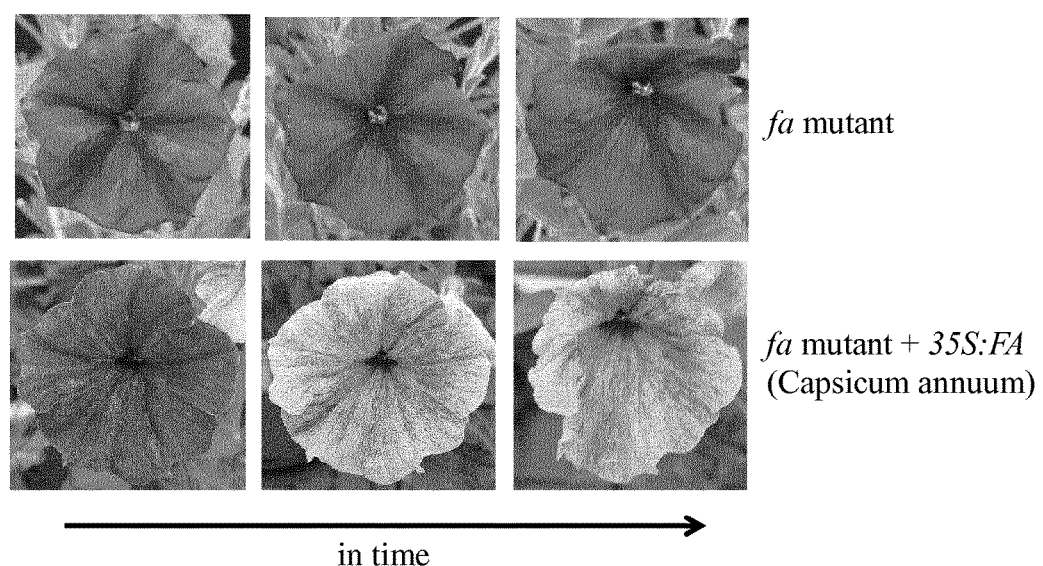

In petunia a complementation assay was performed to investigate the effect of a mutation in the FA gene on fading. The FA gene was mutated by a dTPh1 transposon insertion. A fading mutant petunia plant that contains an insertion in the FA promoter, hence no fading phenotype, was stable transformed with the FA coding sequence under the constitutive 35S promoter. In short, the FA cDNA was PCR amplified from a non fading petunia line (V74) and cloned into a vector containing the cauliflower mosaic virus promoter (35S) and the kanamycin gene for transgene selection. The clone with the correct coding sequence was multiplied in E. coli and subsequently transformed into Agrobacterium tumefaciens AGL0. Leaf tissue from the non fading V74 petunia line was used for Agrobacterium-mediated transformation. The resulting explants were selected for the presence of transgene and those plants containing the transgene showed restoration of the fading phenotype indicating that FA is the gene responsible for fading (FIG. 3A)

To complement the fading phenotype with the Capsicum annuum FA gene, the genomic FA gene from the fading Mavis and Zulu Pepper variety was cloned in the same cloning vector containing the 35S promoter and kanamycin selection marker same plant transformation was followed and Agrobacterium-mediated transformation was used to introduce the Pepper fading gene into petunia V74. The resulting explants were selected for the presence of transgene and those plants containing the transgene showed restoration of the petunia fading phenotype (FIG. 3B).

Experiments show that the petunia fa mutant fading phenotype can be complemented by the FA gene. Results show that the Capsicum annuum FA gene (FIG. 3B) and the petunia FA (FIG. 3A) gene are functionally exchangeable. The non-fading phenotype in petunia was rescued by complementation of non-fading, fa mutant, petunia plants with the FA gene of pepper (Capsicum annuum) transcribed from the strong constitutively 35S promoter. The stable transformed plants, comprising the FA gene, harbour flowers that fade at early stages of development whereas the control plants, comprising a mutated fa gene do not show fading.

Determination of Anthocyanins Concentration in Pepper Fruits

In order to determine the concentration of anthocyanin in pepper fruits, absorption spectroscopy at wavelength of 530 nm was performed. The higher the absorption value measured, the higher the concentration of anthocyanins in the fruit. Mature and immature fruits having a fully functional FA gene (Zulu control) and mature and immature fruits wherein the FA gene was silenced using VIGS (Zulu VIGS FA) were used. The VIGS silencing of the FA gene results in a reduced FA gene expression. Fresh fruits (2-4 fruits per group) were cut in small pieces and frozen in liquid nitrogen. The frozen samples a grinded with liquid nitrogen using a mortar and pestle. Add 5 volumes (based on weight) of extraction buffer, comprised of 45% methanol and 5% acetic acid and mix thoroughly. Centrifuge at 12,000×g for 5 min at room temperature and transfer the supernatant to a new tube. Then centrifuge at 12,000×g for 5 min at room temperature and transfer the supernatant to new tube. Measure absorbance at 530 nm per sample to determine the concentration of anthocyanins in the fruits.

Figure 4:
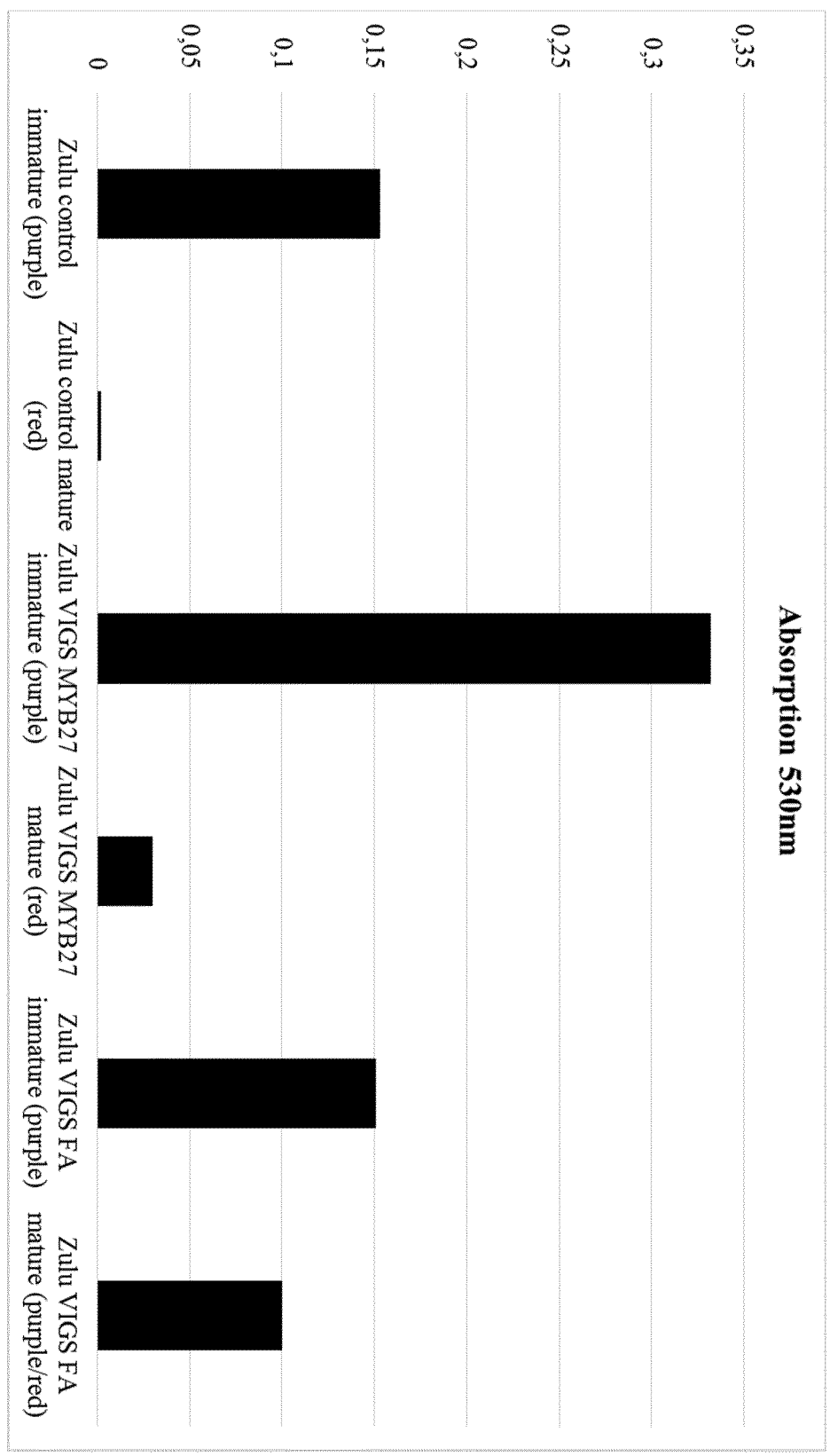
FIG. 4: shows the concentration of anthocyanins in mature and immature pepper fruits (Zulu). Mature and immature fruits having a fully functional FA gene and MYB gene (Zulu control) and mature and immature fruits wherein the FA gene or MYB gene was silenced using VIGS (VIGS FA of VIGS MYB) were used. When the FA gene was VIGS silenced, the FA gene expression is reduced, resulting in a high anthocyanins concentration in both the immature and mature fruits. When the MYBgene was VIGS silenced, the MYB gene expression is reduced, resulting in a high anthocyanins concentration in the immature fruits.

Both immature fruits of the control and VIGS FA group were purple and results show (FIG. 4) that both fruits of these groups show similar high absorption values, and therefore comprise high anthocyanin content. The mature control fruits were red and resulted in a drop in absorption, representing that almost no to a low concentration of anthocyanins were present in these fruits. In the mature VIGS FA fruits, which were purple having red patches, only a slight drop absorption was detected in comparison to the immature VIGS fruits, and again high absorption levels were measured. This result indicates that in mature VIGS FA fruits, the anthocyanins remain present at high levels and that anthocyanin degradation is reduced by reduced FA gene expression.

FA Gene and FA Protein Sequence Alignments

The similarity of the FA gene and FA protein, the MYB gene and MYB protein among Solanaceae was determined using multiple alignment software. The sequences of FA genes (coding sequence) of pepper (Capsicum annuum) SEQ ID No.1, tomato (Solanum lycopersicum) SEQ ID No.3, eggplant (Solanum_melongena) SEQ ID No.5, and petunia (Petunia_axillaris-1, Petunia_axillaris-2, Petunia_axillaris-3), respectively SEQ ID No.7, SEQ ID No.9, and SEQ ID No.11 were determined. The sequences of FA proteins of pepper (Capsicum annuum) SEQ ID No.2, tomato (Solanum lycopersicum) SEQ ID No.4, eggplant (Solanum_melongena) SEQ ID No.6, and petunia (Petunia_axillaris-1, Petunia_axillaris-2, Petunia_axillaris-3), respectively SEQ ID No.8, SEQ ID No.10 and SEQ ID No.12 were determined. Both FA nucleotide (Table 1) and FA protein (Table 2) sequence show high similarity among Solanaceae.

TABLE 1

Percent Identity Matrix FA gene

| | 1. | 2. | 3. | 4. | 5. | 6. |
|---|---|---|---|---|---|---|
| 1. Petunia_axillaris-1 | 100.00 | 78.21 | 78.08 | 77.98 | 76.86 | 77.27 |
| 2. Petunia_axillaris-2 | 78.21 | 100.00 | 90.62 | 87.29 | 86.22 | 86.36 |
| 3. Petunia_axillaris-3 | 78.08 | 90.62 | 100.00 | 86.90 | 85.82 | 86.51 |
| 4. Capsicum_annuum | 77.98 | 87.29 | 86.90 | 100.00 | 90.24 | 91.04 |
| 5. Solanum_lycopersicum | 76.86 | 86.22 | 85.82 | 90.24 | 100.00 | 91.75 |
| 6. Solanum_melongena | 77.27 | 86.36 | 86.51 | 91.04 | 91.75 | 100.00 |

TABLE 2

Percent Identity Matrix FA protein

| | 1. | 2. | 3. | 4. | 5. | 6. |
|---|---|---|---|---|---|---|
| 1. Petunia_axillaris-1 | 100.00 | 74.93 | 73.47 | 74.71 | 73.52 | 73.02 |
| 2. Petunia_axillaris-2 | 74.93 | 100.00 | 87.89 | 84.78 | 82.81 | 84.67 |
| 3. Petunia_axillaris-3 | 73.47 | 87.89 | 100.00 | 82.38 | 80.41 | 82.67 |
| 4. Capsicum_annuum | 74.71 | 84.78 | 82.38 | 100.00 | 86.16 | 87.91 |
| 5. Solanum_lycopersicum | 73.52 | 82.81 | 80.41 | 86.16 | 100.00 | 88.21 |
| 6. Solanum_melongena | 73.02 | 84.67 | 82.67 | 87.91 | 88.21 | 100.00 |

Furthermore, the sequences of MYB genes (coding sequence) of pepper (*Capsicum annuum*) SEQ ID No.1, tomato (*Solanum lycopersicum*) SEQ ID No.3, and petunia (Petunia_axillaris-1) SEQ ID No.7 were determined. The sequences of MYB proteins of pepper (*Capsicum annuum*) SEQ ID No.2, tomato (*Solanum lycopersicum*) SEQ ID No.4, and petunia (Petunia_axillaris-1) SEQ ID No.12 were determined. As for FA gene and protein sequences, also both MYB nucleotide and protein (Table 3 and 4) sequence show high similarity among Solanaceae.

TABLE 3

Percent Identity Matrix MYB gene

|   | 1. | 2. | 3. |
|---|---|---|---|
| 1. Petunia_axillaris-1 | 100.00 | 84.39 | 84.85 |
| 2. Capsicum_annuum | 84.39 | 100.00 | 91.19 |
| 3. Solanum_lycopersicum | 84.85 | 91.19 | 100.00 |

TABLE 4

Percent Identity Matrix MYB protein

|   | 1. | 2. | 3. |
|---|---|---|---|
| 1. Petunia_axillaris-1 | 100.00 | 83.72 | 84.00 |
| 2. Capsicum_annuum | 83.72 | 100.00 | 87.28 |
| 3. Solanum_lycopersicum | 84.00 | 87.28 | 100.00 |

The invention claimed is:

1. A Solanaceae plant for producing fruits rich in anthocyanins concentration, wherein said plant comprises a fading gene (FA gene) that encodes for a fading protein (FA protein), wherein the FA protein has at least 90% amino acid sequence identity with SEQ ID NO: 2, SEQ ID NO: 4, SEQ ID NO: 6, SEQ ID NO: 8, SEQ ID NO: 10, or SEQ ID NO: 12, and wherein said FA gene comprises a non-natural mutation resulting in a reduced expression level or reduced activity of FA protein as compared to a Solanaceae plant wherein no such mutation is present, wherein the Solanaceae plant is selected from the group consisting of *Capsicum annuum, Solanum lycopersicum, Solanum melongena*, and *Petunia_axillaris*.

2. The Solanaceae plant according to claim 1, wherein the fruits of said plant are comprised of a peel that is substantially of purple colour or blue colour.

3. The Solanaceae plant according to claim 1, wherein the fruits of said plant are comprised of a peel and fruit flesh that is substantially of purple or blue colour.

4. The Solanaceae plant according to claim 1, wherein during development of the fruits of said plant comprise at least 50% higher concentration of anthocyanin in a peel as compared to a peel of the fruits obtained from the Solanaceae plant wherein no such mutation is present.

5. The Solanaceae plant according to claim 1, wherein degradation of anthocyanin during development of the fruits is reduced by at most 50% as compared to the anthocyanin concentration of fruits obtained from the Solanaceae plant wherein no such mutation is present.

6. The Solanaceae plant according to claim 1, wherein the Solanaceae plant is *Capsicum annuum* and:

said FA gene comprises a coding sequence that has at least 90% nucleotide sequence identity with SEQ ID NO: 1; and said FA gene encodes for the FA protein that has at least 90% amino acid sequence identity with SEQ ID NO: 2.

7. The Solanaceae plant according to claim 1, wherein the Solanaceae plant is *Solanum lycopersicum* and:

said FA gene comprises a coding sequence that has at least 90% nucleotide sequence identity with SEQ ID NO: 3; and said FA gene encodes for the FA protein that has at least 90% amino acid sequence identity with SEQ ID NO: 4.

8. The Solanaceae plant according to claim 1, wherein the Solanaceae plant is *Solanum melongena* and:

said FA gene comprises a coding sequence that has at least 90% nucleotide sequence identity with SEQ ID NO: 5; and said FA gene encodes for the FA protein that has at least 90% amino acid sequence identity with SEQ ID NO: 6.

9. The Solanaceae plant according to claim 1, wherein the Solanaceae plant is a *Petunia_axillaris* and:

said FA gene comprises a coding sequence that has at least 90% nucleotide sequence identity respectively with SEQ ID NO: 7, SEQ ID NO: 9, or SEQ ID NO: 11; and said FA gene encodes for the FA protein that has at least 90% amino acid sequence identity with SEQ ID NO: 8, SEQ ID NO: 10, or SEQ ID NO: 12.

10. The Solanaceae plant according to claim 1, wherein:

the mutation in the FA gene is a frameshift mutation in the FA gene or a stop codon in the FA gene, or the mutation in the FA gene encodes an amino acid substitution in the encoded protein.

11. The Solanaceae plant according to claim 1, wherein said Solanaceae plant further comprises a mutation in a MYB gene that encodes for a MYB protein resulting in a reduced expression level or reduced activity of MYB protein as compared to a wild-type Solanaceae plant wherein no mutation in the MYB gene is present, wherein the MYB protein has at least 70% amino acid sequence identity with SEQ ID NO: 14.

12. The Solanaceae plant according to claim 11, wherein the Solanaceae plant is *Capsicum annuum* and:

said MYB gene comprises a coding sequence that has at least 90% nucleotide sequence identity with SEQ ID NO: 13; and said MYB gene encodes for the MYB protein that has at least 90% amino acid sequence identity with SEQ ID NO: 14.

13. The Solanaceae plant according to claim 11, wherein the Solanaceae plant is *Solanum lycopersicum* and:

said MYB gene comprises a coding sequence that has at least 90% nucleotide sequence identity with SEQ ID NO: 15; and said MYB gene encodes for the MYB protein that has at least 90% amino acid sequence identity with SEQ ID NO: 16.

14. The Solanaceae plant according to claim 11, wherein the Solanaceae plant is a petunia plant and:

said MYB gene comprises a coding sequence that has at least 90% nucleotide sequence identity with SEQ ID NO: 17; and said MYB gene encodes for the MYB protein that has at least 90% amino acid sequence identity with SEQ ID NO: 18.

15. The Solanaceae plant according to claim 11, wherein said mutation in the MYB gene is a non-natural mutation.

16. The Solanaceae plant according to claim 1, wherein the fruits have an increased shelf life.

17. A method for providing the Solanaceae plant according to claim 1, the method comprising the steps of:

a) introducing the mutation in the fading gene (FA gene), wherein said FA gene comprises a coding sequence that has at least 70% nucleotide sequence identity with SEQ ID NO: 1;

b) determining a reduction of the endogenous level of FA protein and/or FA mRNA in the Solanaceae plant; and c) selecting the Solanaceae plant that produces fruits that are rich in anthocyanins.

18. The method according to claim 17, wherein step a) further comprises introducing a mutation in a MYB gene, wherein said MYB gene comprises a coding sequence that has at least 70% nucleotide sequence identity with SEQ ID NO: 13.

19. The method according to claim 17, wherein step b) of the method further comprises determining a reduction of the endogenous level of MYB protein and/or MYB mRNA in the Solanaceae plant.

20. The method according to claim 17, wherein mutation of the FA gene and/or a MYB gene is effected by gene editing techniques.

* * * * *

UNITED STATES PATENT AND TRADEMARK OFFICE
CERTIFICATE OF CORRECTION

PATENT NO. : 11,401,525 B2
APPLICATION NO. : 17/055698
DATED : August 2, 2022
INVENTOR(S) : Cornelis Walter Verweij et al.

Page 1 of 1

It is certified that error appears in the above-identified patent and that said Letters Patent is hereby corrected as shown below:

On the Title Page

Column 2, Item (56) Other Publications, Line 4, delete "Passed" and insert -- Passeri --

In the Claims

Column 55, Line 64, Claim 1, delete "Petunia_axillaris." and insert -- Petunia axillaris. --

Column 57, Line 22, Claim 9, delete "Petunia_axillaris" and insert -- Petunia axillaris --

Signed and Sealed this
Twenty-seventh Day of September, 2022

Katherine Kelly Vidal
*Director of the United States Patent and Trademark Office*